(12) United States Patent
Kim et al.

(10) Patent No.: US 11,428,660 B2
(45) Date of Patent: Aug. 30, 2022

(54) METAL OXIDE NANOFIBERS INCLUDING FUNCTIONALIZED CATALYST USING CHITOSAN-METAL COMPLEXES, AND MEMBER FOR GAS SENSOR, AND GAS SENSOR USING THE METAL OXIDE NANOFIBERS, AND METHOD OF FABRICATING THE SAME

(71) Applicant: Korea Advanced Institute of Science and Technology, Daejeon (KR)

(72) Inventors: Il-Doo Kim, Daejeon (KR); Yong Jin Jeong, Daejeon (KR); Won-Tae Koo, Daejeon (KR); Ji-Soo Jang, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 642 days.

(21) Appl. No.: 16/448,546

(22) Filed: Jun. 21, 2019

(65) Prior Publication Data
US 2019/0391101 A1    Dec. 26, 2019

(30) Foreign Application Priority Data

Jun. 22, 2018 (KR) .................. 10-2018-0071884

(51) Int. Cl.
| | |
|---|---|
| *G01N 27/12* | (2006.01) |
| *D01D 1/02* | (2006.01) |
| *D01D 5/00* | (2006.01) |
| *D01F 9/10* | (2006.01) |
| *G01N 33/497* | (2006.01) |

(52) U.S. Cl.
CPC .............. *G01N 27/127* (2013.01); *D01D 1/02* (2013.01); *D01D 5/003* (2013.01); *D01F 9/10* (2013.01); *G01N 33/497* (2013.01); *G01N 2033/4975* (2013.01)

(58) Field of Classification Search
CPC ...... G01N 27/127; G01N 33/497; D01D 1/02; D01D 5/003; D01F 9/10; B82Y 30/00
See application file for complete search history.

(56) References Cited

U.S. PATENT DOCUMENTS

| | | | |
|---|---|---|---|
| 2005/0011827 A1* | 1/2005 | Koslow .................. | D21H 13/50 210/508 |
| 2007/0207186 A1* | 9/2007 | Scanlon .................. | B29C 55/26 623/1.42 |
| 2014/0027938 A1* | 1/2014 | Swatloski ............ | D01D 5/0046 264/10 |
| 2016/0130370 A1* | 5/2016 | Meredith, III ............ | C08L 5/08 428/401 |
| 2016/0263554 A1* | 9/2016 | Grubbs .................... | C02F 1/444 |
| 2016/0334359 A1* | 11/2016 | Kim .............................. | 27/407 |
| 2017/0200943 A1* | 7/2017 | Kawakami ............. | H01G 11/40 |

* cited by examiner

*Primary Examiner* — Francis C Gray

(74) *Attorney, Agent, or Firm* — Verrill Dana, LLP

(57) ABSTRACT

Disclosed are a member for a gas sensor, a gas sensor using the member, and a method of fabricating the same. Specifically, disclosed are a member for a gas sensor using a metal oxide nanofiber material in which nanocatalysts have been uniformly bound and functionalized using chitosans with which nanoparticle catalysts have been combined, a gas sensor using the member, and a method of fabricating the same.

10 Claims, 22 Drawing Sheets

METAL OXIDE NANOFIBERS INCLUDING FUNCTIONALIZED CATALYST USING CHITOSAN-METAL COMPLEXES, AND MEMBER FOR GAS SENSOR, AND GAS SENSOR USING THE METAL OXIDE NANOFIBERS, AND METHOD OF FABRICATING THE SAME

CROSS REFERENCE TO RELATED APPLICATION

This application is based on and claims priority under 35 U.S.C. 119 to Korean Patent Application No. 10-2018-0071884, filed on Jun. 22, 2018, in the Korean Intellectual Property Office, the disclosures of which is herein incorporated by reference in their entireties.

BACKGROUND OF THE INVENTION

1. Technical Field

The present invention relates to a member for a gas sensor, a gas sensor using the member, and a method of fabricating the same and, more particularly, to metal oxide nanofibers in which a nanocatalyst has been uniformly bound and functionalized by bonding a metal catalyst of several nanometers in size to chitosan, mixing the chitosan with an electrospinning solution, and then performing an electrospinning and high-temperature thermal treatment process, a member for a gas sensor using the nanofibers, a gas sensor using the member, and a method of fabricating the same.

2. Description of the Related Art

As health management becomes important, there is an emerging need for a technology capable of simple daily diagnosis of diseases, and a real-time monitoring system capable of early prevention of diseases.

Most of the present disease diagnosis technologies have disadvantages in that they make patients inconvenient because they are invasive, and that they are expensive and inefficient because a patient must personally visit a hospital. Accordingly, one of next-generation diagnosis technologies capable of solving such problems is a gas sensor for exhaled breath analysis. The gas sensor for diagnosing a disease by analyzing expiration has been in the spotlight because they have advantages of non-invasiveness, simple fabrication methods, and portability. The principle of the gas sensor for exhaled breath analysis is to identify whether a disease is present by checking concentrations of specific gas species included in a person's expiration. When compared with a healthy person, a person taken with a specific disease has 2 to 10 times higher biomarker gas concentration in the expiration. For example, acetone gas is one of the biomarker gases for diabetes. A diabetic patient has acetone gas (1.8 part per million (ppm)) concentration 2 to 6 times greater than that of a healthy person (300 to 900 part per billion (ppb)) in expiration. Accordingly, if a gas sensor capable of detecting such a biomarker gas included in a person's expiration is developed, a disease can be early diagnosed effectively. However, a biomarker gas within a person's expiration is emitted in a very low level from 10 ppb to 10 ppm, and several hundred or more are gas species are included in a person's expiration. Accordingly, the gas sensor for exhaled breath analysis must have high sensitivity and excellent selectivity. Furthermore, in order to commercialize a disease diagnosis expiration sensor, overall expenses necessary to develop the gas sensor must be reduced using a cheap material and a simple process.

Furthermore, an example of a required real-time monitoring system for disease prevention is a system capable of diagnosing air quality within a building, for preventing sick house syndrome. Among several gas species that cause the sick house syndrome, formaldehyde gas has the highest toxicity to the extent that in most countries, it is regulated to a very small amount of 0.2 ppm or less based on its concentration. Practically, if a person is exposed to formaldehyde of 0.2 ppm, he or she may experience a respiratory disorder. Formaldehyde concentration of 30 ppm or higher can cause severe disease, such as pulmonary angioneurotic edema. Accordingly, there is an urgent need to develop a system capable of selectively detecting a very small amount of formaldehyde in early stages. However, a formaldehyde sensor must have excellent selectivity in addition to high sensitivity characteristic, because indoor air contains a variety of gas species in addition to formaldehyde. In many companies and research laboratories, efforts are continuously made to develop a gas sensor capable of selectively detecting formaldehyde gas of 0.2 ppm because the gas sensor has not been developed so far.

Among various substances which may be used as a sensing material of the gas sensor, metal oxide is most frequently used as the sensing material for gases because it has a simple detection principle, can be easily fabricated, and has an excellent application possibility. A chemiresistive gas sensor based on a metal oxide semiconductor detects gas by measuring a change in resistance according to the adsorption and desorption of the gas occurring on a surface of a sensing material. Accordingly, in order to improve the detection ability of the gas sensor, a change in resistance needs to be increased by increasing the active surface area of the sensing material. A 1-dimensional nanofiber produced by electrospinning has been actively researched as a sensing material of the chemiresistive gas sensor in that it has a wide specific surface area and facilitates the diffusion of gas through pores formed by an intertwine structure. In this case, if additional pores are formed in a nanofiber, the sensitivity of a nanofiber-based gas sensor can be effectively increased because a target gas can infiltrate the nanofiber and respond. Furthermore, in order to realize the high sensitivity and high selectivity of the nanofiber-based gas sensor, a reaction between a specific gas and a sensing material needs to be increased and the adsorption and detachment reaction of gas need to be accelerated by decorating a catalyst to a surface of nanofibers. If the size of catalyst particles is large or agglomeration occurs between the catalyst particles, however, it is difficult to realize a gas sensor having excellent performance because an effect of the catalyst is greatly reduced. Agglomeration between the catalyst particles may occur very easily because a operation temperature of a metal oxide-based gas sensor is a high temperature of 300 degrees Celsius or more. Accordingly, a catalyst binding method capable of maximizing an effect of catalyst by uniformly distributing the catalyst of a nano size on a surface of nanofibers needs to be developed.

Research of the above-described method of uniformly binding catalyst of a nano size on a surface of nanofibers has been actively carried out. A known catalyst synthesis method is to synthesize catalyst particles using polyol synthesis. Catalyst particles may be synthesized in a small size using this method, but there is a disadvantage in that agglomeration easily occurs between the catalyst particles. Substances used to overcome the disadvantage include a metal-organic framework and apoferritin, that is, animal proteins. Particularly, if catalyst particles are synthesized using apoferritin, such a catalyst binding method of a gas sensor sensing material has been considered to be an optimized method because the catalyst particles are synthesized in a very small size (2 to 3 nm) and have excellent dispersibility. However, many experts consider that it is difficult to commercialize the method due to a very high price and a complicated process despite excellent performance of apoferritin. Accordingly, research of a catalyst binding method for realizing a high effect using a cheap and simple process is a great issue so far. If such a catalyst binding method is realized, cooperation with several companies is possible and further progress to commercialization may be possible because a gas sensor capable of monitoring indoor air in real time in addition to a high performance gas sensor for exhaled breath analysis can be simply fabricated.

SUMMARY OF THE INVENTION

An embodiment of the present invention provides a method of mixing chitosan-nanocatalyst complexes, composed by combining catalyst metal particles of a nano size and chitosan with a electrospinning solution, synthesizing metal oxide precursor/polymers complex nanofibers to which chitosan-nanocatalyst complexes have been uniformly bound, and then synthesizing metal oxide nanofibers in which nanocatalysts have been uniformly decorated and functionalized through high-temperature thermal treatment.

Particularly, the nanocatalysts of the chitosan-nanocatalyst complexes have an advantage in that they do not agglomerate together and are well dispersed due to a repulsive force between the chitosans because they are synthesized to a very small size of 1 to 100 nm. Furthermore, in the high-temperature thermal treatment process, the remaining chitosans suppress the growth of the metal oxide particles during the thermal treatment process because a thermal decomposition temperature of the chitosan is higher than a crystallization temperature of the metal oxide precursor. Accordingly, metal oxide of small grains can be synthesized. Furthermore, an inorganic component left over in chitosans during calcination also effectively suppress the growth of the metal oxide grains even in a higher temperature. In this case, the synthesized metal oxide of small grains generates a further enhanced change in resistance because a change in the electron depletion layer within the metal oxide is maximized when a gas reaction occurs. Furthermore, organic matters included in the chitosan are decomposed during the thermal treatment process to generate pores within the metal oxide nanofiber. Such pores facilitate the diffusion of gas to lead to high sensitivity and fast sensing speed. Furthermore, the inorganic components left over as the residues of the chitosan are oxidized to form a plurality of heterojunctions with the metal oxide, thus playing an electronic sensitizer role. That is, there are proposed a technology for synthesizing metal oxide nanofiber sensing materials including functionalized catalysts, which significantly increases a gas sensing characteristic by forming an electronic sensitization catalyst, including nanocatalysts of high dispersibility, porous metal oxide of small particles, and a plurality of heterojunctions, at once using chitosan-nanocatalyst complexes which can be synthesized cheaply and simply, and a gas sensor application technology using the same.

That is, there is proposed sensing material synthesis technology which has not been conventionally proposed and is cheap, but has high efficiency, that is, a member for a gas sensor capable of selectively sensing a very small amount of gas, a gas sensor using the member, and a method of fabricating the same from the effects of the above-described chitosan-nanocatalyst complexes.

In an aspect, there are provided a sensing material in which nanocatalysts are uniformly decorated to metal oxide nanofibers and functionalized, and a small particle size, pores and the electronic sensitizer role of residues are realized at once by synthesizing chitosan-nanocatalyst complexes composed by combining catalyst metal particles of a nano size and chitosans, mixing the synthesized complexes with a electrospinning solution, and then performing electrospinning and a post-thermal treatment process, and a method of fabricating a member for a gas sensor using the sensing material. Embodiments of the present invention provides the sensing material and the method of fabricating a member for a gas sensor using the sensing material, and further provides a method of fabricating metal oxide nanofibers including functionalized catalysts, including the steps of:

(a) preparing a solution in which chitosan-nanocatalyst complexes have been dissolved;

(b) preparing a solution in which a metal oxide precursor and polymers have been dissolved;

(c) fabricating a electrospinning solution by mixing the solution in which the chitosan-nanocatalyst complexes have been dissolved and the solution in which the metal oxide precursor and polymers have been dissolved;

(d) forming complex nanofibers, including the chitosan-nanocatalyst complexes, the metal oxide precursor, and the polymers, by electrospinning of the electrospinning solution;

(e) thermally decomposing the polymers and chitosans by thermally treating the complex nanofibers at a high temperature, oxidizing the metal oxide precursor, and fabricating metal oxide nanofibers in which nanocatalysts have been uniformly bound to the nanofibers and functionalized; and (f) grinding the metal oxide nanofibers in which the catalysts have been functionalized, dispersing the results in ethanol, and coating the results on a sensor electrode for a chemiresistive gas sensor.

In this case, in step (a), the chitosan is linear polysaccharide containing a large amount of nitrogen, and has the property that the chitosan is combined with metal ions in the aqueous state. Representative metal salts including the metal ions which may be combined with the chitosan include platinum(IV) chloride, platinum(II) acetate, gold(I, III) chloride, gold(III) acetate, silver chloride, silver acetate, Iron(III) chloride, Iron(III) acetate, nickel(II) chloride, nickel(II) acetate, ruthenium(III) chloride, ruthenium acetate, iridium (III) chloride, iridium acetate, tantalum(V) chloride, palladium(II) chloride, lanthanum(III) acetate, copper(II) sulfate, rhodium(III) chloride, and so on. After the metal ions and the chitosans are combined by adding the above-described metal salts to the chitosan aqueous solution, when a reducing agent is added, the metal ions are reduced to Pt, Au, Ag, Fe, Ni, Ru, Ir, Ta, Pd, La, Cu and Rh to form chitosan-metal complexes. Representative reducing agents which may be used in the process may include sodium borohydride ($NaBH_4$), lithium aluminum hydride ($LiAlH_4$), nascent (atomic) hydrogen, zinc-mercury amalgam (Zn(Hg)), oxalic acid ($C_2H_2O_4$), formic acid (HCOOH), ascorbic acid ($C_6H_8O_6$), sodium amalgam, diborane, iron(II) sulfate, and so on. The metal particle of the formed chitosan-metal complex has a diameter range of 1 to 100 nm and is called a chitosan-nanocatalyst complex because it functions as a catalyst. The metal particle shows excellent dispersibility due to a repulsive force between chitosans, and has a characteristic capable of adjusting the size of the metal particles depending on the type of metal salt, concentration of chitosans, a concentration of metal salts, etc. Furthermore, if chitosan-nanocatalyst complexes are formed by injecting two or more different metal salts at the same time, metal alloy catalyst particles may be synthesized.

Furthermore, in step (b), the polymer is a template for forming metal oxide nanofibers by performing electrospinning, and representatively may include polymethylmethacrylate (PMMA), polyvinylpyrrolidone (PVP), polyvinylacetate (PVAc), polyvinylalcohol (PVA), polyacrylonitrile (PAN), polyethylene oxide (PEO), polypropylene oxide (PPO), polyethylene oxide copolymer, polypropylene oxide copolymer, polycarbonate (PC), polyvinylchloride (PVC), polycaprolactone, polyvinylidene fluoride, etc. The metal oxide precursor is a metal salt for forming metal oxide through post-thermal treatment. Representative metal salts may include forms, such as acetate, chloride, acetylacetonate, nitrate, methoxide, ethoxide, butoxide, isopropoxide, and sulfide including metal salts.

Furthermore, step (c) is the step of fabricating a complex electrospinning solution composed of the chitosan-nanocatalyst complex/metal oxide precursor/polymers by mixing the chitosan-nanocatalyst complexes, synthesized in step (a), with the solution synthesized in step (b). The complex electrospinning solution is fabricated by slowly adding the solution in which the chitosan-nanocatalyst complexes have been dissolved in the state in which the solution synthesized in step (b) is stirred. If the electrospinning solution is to be fabricated, a concentration of the nanocatalysts of the chitosan-nanocatalyst complexes may be varied in the range of 0.001 to 50 wt % with respect to the metal oxide.

Furthermore, step (d) is the step of synthesizing the complex nanofibers composed of the chitosan-nanocatalyst complex/metal oxide precursor/polymers by electrospinning of the complex electrospinning solution synthesized in step (c). In this case, the chitosan-nanocatalyst complexes are uniformly distributed on the inside and a surface of the complex nanofibers due to excellent dispersibility of the chitosan-nanocatalyst complexes.

Furthermore, in step (e), the organic components of the chitosans and the polymers are thermally decomposed, the metal oxide precursor is oxidized and crystallized, and the nanocatalysts combined with the chitosans are uniformly bound to the nanofibers through the high-temperature thermal treatment of the complex nanofibers synthesized in step (d). Accordingly, an effect of the catalyst is maximized because agglomeration does not occur between the catalyst nanoparticles. In this case, the nanocatalyst may be oxidized and transposed into at least one nanocatalyst of Pt, PtO, $PtO_2$, Au, $Au_2O_3$, Ag, $Ag_2O$, $Fe_2O_3$, NiO, $RuO_2$, $IrO_2$, $Ta_2O_5$, PdO, $PdO_2$, $La_2O_3$, CuO and $Rh_2O_3$. The metal oxide precursor may be oxidized and composed of one or two or more complex materials selected from ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $ZrO_2$, $Al_2O_3$, $B_2O_3$, $V_2O_5$, $Cr_2O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $MnO_2$, $InTaO_4$, ITO, IZO, $InTaO_4$, MgO, $Ga_2O_3$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, and $Ba_{0.5}Sr_{0.5}Co_{0.8}Fe_{0.2}O_{3-7}$. Furthermore, in the thermal treatment process, uniformly distributed chitosan chains suppress the growth of the metal oxide crystal grains because the thermal decomposition temperature of the chitosan is higher than the crystallization and particle growth temperature of the metal oxide precursor. Thereafter, the chitosans are finally thermally decomposed, and pores having a size range of 1 to 50 nm are left in the nanofibers to form porous metal oxide nanofibers. Accordingly, the diffusion of gas is facilitated upon reaction. Furthermore, Mg, Fe, etc., that is, inorganic components derived in the process of extracting chitosans from the shell of a crustacean and synthesizing the chitosans, are oxidized after the thermal treatment to form MgO, $Fe_2O_3$, FeO, $Fe_3O_4$. The oxides have a range of 0.00001 to 10 wt % with respect to the metal oxide, and form heterojunctions with the metal oxide, thus playing an electronic sensitizer role.

Furthermore, step (f) is the step of finely dispersing the metal oxide nanofibers in which the nanocatalysts synthesized in step (e) have been functionalized, dispersing them in ethanol, and then coating the dispersion solution on a sensor electrode for a variable resistance type gas sensor using at least one coating process of spin coating, drop coating, inkjet printing and dispensing. Any coating method may be used if a sensing material can be uniformly coated on the sensor electrode.

The synthesized sensing material has an advantage in that it can significantly increase the sensing characteristic due to the effect of the chitosan-nanocatalyst complexes because the nanocatalysts have been uniformly bound and functionalized to the nanofibers, pores are formed in the nanofibers to facilitate gas diffusion, the area of an electron depletion layer is increased by suppressing the growth of the metal oxide particles, and the sensing material plays an electronic sensitizer role because the inorganic component of the chitosan is oxidized.

BRIEF DESCRIPTION OF THE DRAWINGS

The accompanied drawings, which are included as part of the detailed description in order to help the understanding of the present invention, provide embodiments of the present invention and describe the technical characteristics of the present invention along with the detailed description.

DESCRIPTION OF REFERENCE NUMERALS

Figure 1:
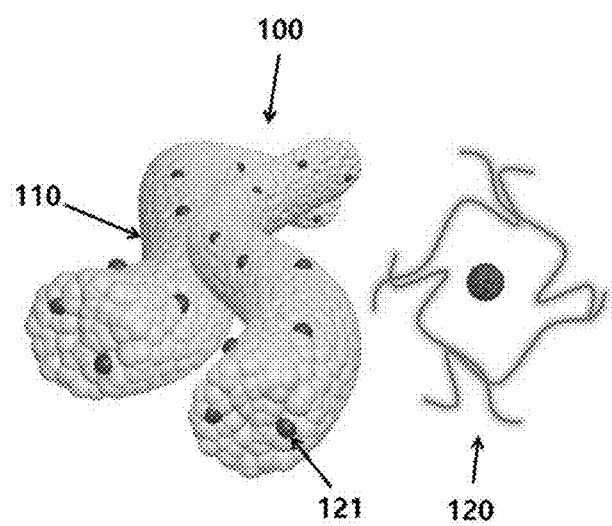
FIG. 1 is a diagram of a member for a metal oxide nanofiber gas sensor in which nanocatalysts are uniformly bound and functionalized according to an embodiment of the present invention.

100: Member for metal oxide nanofiber gas sensor in which nanocatalysts have been functionalized
110: Metal oxide nanofiber in which nanocatalysts have been functionalized
120: Chitosan-nanocatalyst complex
121: Nanocatalyst functionalized from chitosan-nanocatalyst complex

DETAILED DESCRIPTION

The present invention may be modified in various ways and may have various embodiments. Hereinafter, specific embodiments of the present invention will be illustrated in the accompanying drawings and described in detail.

In describing the present invention, a detailed description of the known technologies will be omitted if it is deemed to make the gist unnecessarily vague.

Terms, such as the first and the second, may be used to describe various elements, but the elements should not be restricted by the terms. The terms are used to only distinguish one element from the other element.

In the present invention, chitosan-nanocatalyst complexes are formed by combining catalysts of a nano size with chitosans. The chitosan-nanocatalyst complexes are combined with electrospinning. Complex nanofibers to which chitosan-nanocatalyst complexes have been uniformly bound are synthesized with nanofibers including a metal oxide precursor and polymers. Thereafter, the organic components of the chitosan and the polymers are decomposed through high-temperature thermal treatment. A metal oxide precursor is oxidized and crystallized. Nanocatalysts combined with the chitosans are uniformly bound to metal oxide nanofibers and functionalized. Oxide formed through the oxidation of the inorganic components of the chitosans forms heterojunctions with the metal oxide.

Particularly, an effect of catalysts is maximized and a sensing characteristic is significantly increased because the nanocatalysts of a very small size are uniformly bound. Furthermore, in the high-temperature thermal treatment process of the complex nanofibers, a thermal decomposition temperature of the chitosans is higher than a crystallization temperature of the metal oxide precursor. Accordingly, metal oxide nanofibers having a small particle size are formed because the chitosans suppress the growth of metal oxide particles. Such a small particle size leads to an increase of sensitivity by maximizing a change in resistance depending on whether gas is present. Furthermore, the pores remained after the organic matter components of the chitosans are decomposed increase reactivity by accelerating the diffusion of gas. Oxide formed by the oxidation of the inorganic components of the chitosan forms heterojunctions with metal oxide and thus, plays an electronic sensitizer role. The above effects are achieved at once using the chitosan having a cheap and simple process. Accordingly, a very small amount of gas can be rapidly detected selectively because the characteristics of a sensor are significantly increased. A variety of types of sensing material groups that enable the detection of various gases can be secured by variously changing the type of nanoparticle catalyst and metal oxide. Particularly, there are disclosed member for a gas sensor capable of mass production, a gas sensor using the member, and a method of fabricating the same because the bonding of nanoparticle catalysts and control of the shape of nanofibers are performed at the same time cheaply and simply through electrospinning and thermal treatment using the chitosans.

Hereinafter, metal oxide nanofibers in which nanocatalysts have been functionalized using chitosan-nanocatalyst complexes, a member for a gas sensor using the metal oxide nanofibers, a gas sensor, and a method of fabricating the same are described in with reference to the accompanying drawings.

An embodiment of the present invention provides a metal oxide nanofiber including functionalized catalysts, wherein metal is bound to the inside and the surface in nano size and functions as a catalyst through high-temperature thermal treatment of a complex nanofiber including chitosan-metal complexes, a metal oxide precursor, and polymers.

According to one aspect, metal particles of the chitosans-metal complex may be configured with one or two or more metals included in a range of 1 to 100 nm in diameter through bonding with chitosan.

According to another aspect, metal particles of the chitosans-metal complex may be uniformly decorated to a nanofiber and functionalized through dispersibility according to a repulsive force between chitosans.

According to yet another aspect, in the metal oxide nanofiber in which the catalysts have been functionalized, the chitosan may be thermally decomposed through high-temperature thermal treatment of the complex nanofiber and forms pores having a size range of 1 to 50 nm in the nanofiber.

According to yet another aspect, in the high-temperature thermal treatment process of the complex nanofiber, a thermal decomposition temperature of the chitosan may be higher than the crystallization temperature of the metal oxide precursor, the chitosans uniformly distributed in the complex nanofiber may suppress a growth of metal oxide particles, and components remaining as residues after the chitosan is decomposed may continue to suppress a growth of metal oxide particles.

According to yet another aspect, the chitosan of the chitosans-metal complex naturally may contain an inorganic component in a process of extracting the chitosan from the shell of a crustacean and synthesizing the chitosan.

According to yet another aspect, in the metal oxide nanofiber in which the catalysts have been functionalized, in the high-temperature thermal treatment process of the complex nanofiber, inorganic components included in the chitosan form heterojunctions with metal oxide.

According to yet another aspect, wt % of the metal included in the chitosans-metal complex may be included in a range of 0.001 to 50 wt % with respect to the metal oxide.

According to yet another aspect, the chitosans-metal complex may be formed by combining the chitosan with metal ions by adding one or two or more metal salts selected from acetate, nitrate, chloride, acetylacetonate, methoxide, ethoxide, butoxide, isopropoxide, and sulfide to a solution in which the chitosan has been dissolved and reducing the metal ions to one or two or more metal particles through reduction treatment.

According to yet another aspect, the metal oxide nanofiber may be configured with one or two or more complex metal oxide materials selected from $ZnO$, $SnO_2$, $WO_3$, $Fe_2O_3$, $Fe_3O_4$, $NiO$, $TiO_2$, $CuO$, $In_2O_3$, $Zn_2SnO_4$, $Co_3O_4$, $PdO$, $LaCoO_3$, $NiCo_2O_4$, $Ca_2Mn_3O_8$, $ZrO_2$, $Al_2O_3$, $B_2O_3$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $MnO_2$, $InTaO_4$, $ITO$, $IZO$, $InTaO_4$, $MgO$, $Ga_2O_3$, $CaCu_3Ti_4O_{12}$, $Ag_3PO_4$, $BaTiO_3$, $SrTiO_3$, $Sr_2Nb_2O_7$, $Sr_2Ta_2O_7$, and $Ba_{0.5}Sr_{0.5}Co_{0.8}Fe_{0.2}O_{3-7}$.

There is provided gas sensor including a sensor electrode on which metal oxide nanofibers including functionalized catalysts have been coated and capable of measuring a change in resistance.

There is provided method of fabricating a metal oxide nanofiber in which catalysts have been functionalized, including the steps of (a) preparing a first solution in which chitosan-metal complexes have been dissolved in, (b) preparing a second solution in which a metal oxide precursor and polymers have been dissolved, (c) fabricating a electrospinning solution by mixing the first solution and the second solution, (d) forming complex nanofibers including the chitosan-metal complexes, the metal oxide precursor, and the polymers by electrospinning of the electrospinning solution, and (e) fabricating a metal oxide nanofiber in which nanocatalysts have been bound to the nanofiber and functionalized by performing thermal treatment on the complex nanofibers at a high-temperature.

According to one aspect, the method of fabricating metal oxide nanofibers in which catalysts have been functionalized may further include the step of (f) dispersing the fabricated metal oxide nanofiber in a solvent by grinding the fabricated metal oxide nanofiber and coating the dispersed oxide nanofiber on a sensor electrode for a variable resistance gas sensor using at least one coating process of spin coating, drop coating, ink-jet printing or dispensing.

According to another aspect, step (a) may include the steps of (a1) preparing a solution in which chitosans have been dissolved, (a2) preparing a solution in which metal ions and the chitosans have been combined by adding metal salts to the solution in which the chitosans have been dissolved, and (a3) reducing the metal ions to metal particles by adding a reducing agent to the solution in which the metal ions and the chitosans have been combined.

According to yet another aspect, in the method of fabricating metal oxide nanofibers in which catalysts have been functionalized, in the step (a2), wt % between the chitosans and the metal salts may be included in a range of 1:0.000001-1.

According to yet another aspect, the reducing agent may include at least one of sodium borohydride ($NaBH_4$), lithium aluminum hydride ($LiAlH_4$), nascent (atomic) hydrogen, zinc-mercury amalgam ($Zn(Hg)$), oxalic acid ($C_2H_2O_4$), formic acid ($HCOOH$), ascorbic acid ($C_6H_8O_6$), sodium amalgam, diborane, and iron (II) sulfate. wt % between the metal ions and the reducing agent may be included in a range of 1:0.000001-1.

According to yet another aspect, in the method of fabricating metal oxide nanofibers in which catalysts have been functionalized, in step (e), metal particles of the chitosan-metal complex may be bound to the nanofiber in a nano size through the thermal treatment and function as catalysts, and repulsive force between the chitosans maximizes an effect of the catalyst by preventing cohesion between the metal particles functioning as the catalysts.

According to yet another aspect, in step (a), two or more types of metal particles may be included in the chitosan-metal complex. In step (e), the two or more types of metal particles may be bound to the nanofiber through the thermal treatment to complexly function and form multiple heterojunctions.

According to yet another aspect, in the method of fabricating metal oxide nanofibers in which catalysts have been functionalized, in step (e), a porous metal oxide nanofiber may be formed by pores formed as the chitosans are thermally decomposed through the thermal treatment, thereby accelerating a diffusion of gas upon reaction.

According to yet another aspect, in the method of fabricating metal oxide nanofibers in which catalysts have been functionalized, in step (e), inorganic components may be included in the metal oxide nanofiber in a wt % ratio of a 0.00001 to 10 wt % range with respect to the metal oxide as residues as the chitosans are thermally decomposed through the thermal treatment.

In embodiments of the present invention, chitosan-nanocatalyst complexes are formed by combining nanocatalysts with chitosans. After a complex electrospinning solution is fabricated by mixing the chitosan-nanocatalyst complexes with a metal oxide precursor/polymer solution, the chitosan-nanocatalyst complexes are uniformly bound to the metal oxide precursor/polymers complex nanofibers by performing electrospinning. Thereafter, the polymer is thermally decomposed, the metal oxide precursor is oxidized and crystallized, and the chitosans are thermally decomposed through a high-temperature thermal treatment process. Accordingly, the nanocatalysts are uniformly bound to the nanofibers and functionalized, so sensing materials for a gas sensor can be synthesized in large quantities.

In this case, due to the effects of the chitosans, an effect of catalysts appearing when gas reacts to the nanofibers can be maximized because the nanocatalysts are uniformly bound. The stability of a gas sensor is improved because catalyst particles do not cohere together even in a high operating temperature. Furthermore, in the high-temperature thermal treatment process, synthesized metal oxide has a small particle size because chitosans chains suppress the growth of the metal oxide particles. This has a characteristic of high sensitivity because a change in resistance depending on whether gas is present is maximized. Furthermore, the chitosans are decomposed to leave pores in the nanofibers. In this case, a sensing characteristic is improved because the diffusion of gas into the nanofibers is facilitated to widened reaction area. Furthermore, an inorganic component naturally included in the chitosan is not decomposed in the thermal treatment process and remains as residues to have an electronic sensitization effect, thereby resulting in a high sensitivity characteristic.

FIG. 1 is a diagram of a member 100 for gas sensor using metal oxide nanofibers 110 in which chitosan-nanocatalyst complexes 120 having nanocatalysts 121 combined with chitosans are decomposed after high-temperature thermal treatment and the nanocatalysts are uniformly bound to nanofibers and functionalized according to an embodiment of the present invention. The nanocatalyst having a very small size of about 3 nm is uniformly bound to the nanofiber and functionalized, thus having an excellent sensing characteristic.

A sensor having excellent sensitivity and selective sensing ability for a specific gas is implemented through the member 100 for a gas sensor using the metal oxide nanofibers including the functionalized catalysts. Accordingly, a biomarker gas included in a person's expiration can be selectively detected using the sensor, thereby enabling early diagnosis and daily diagnosis of a disease. Furthermore, a catalyst characteristic can be effectively controlled by quantitatively adjusting the amount of the catalysts included in the nanofibers. A member for a gas sensor which may be used to detect a variety of gases can be simply fabricated through the synthesis of various types of nanocatalysts/metal oxide complex nanofibers.

Figure 2:
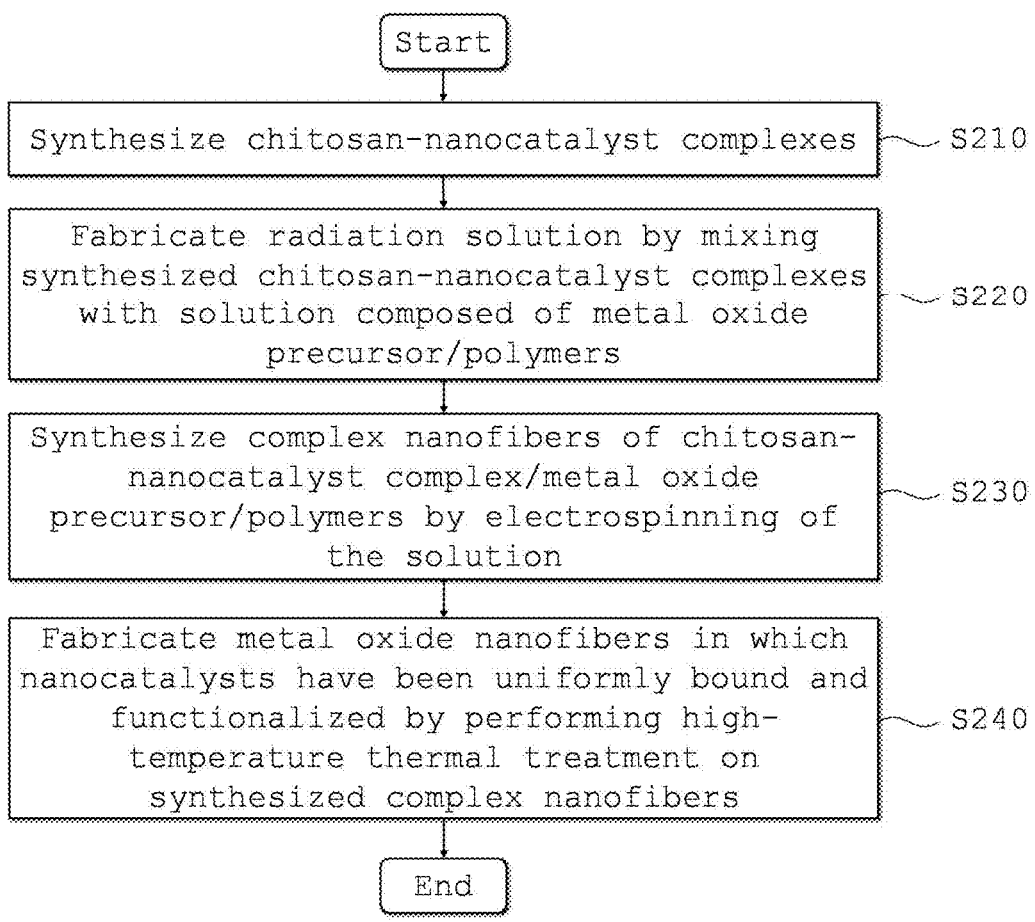
FIG. 2 is a flowchart of a gas sensor fabrication method using metal oxide nanofiber structures in which nanocatalysts have been uniformly bound and functionalized according to an embodiment of the present invention.

FIG. 2 is a flowchart of a gas sensor fabrication method using metal oxide nanofibers in which nanocatalysts have been functionalized according to an embodiment of the present invention. As may be seen from the flowchart, the gas sensor fabrication method may include the step S210 of synthesizing chitosan-nanocatalyst complexes, the step S220 of fabricating a electrospinning solution by mixing the synthesized chitosan-nanocatalyst complexes with a solution composed of a metal oxide precursor/polymers, the step S230 of synthesizing the complex nanofibers of the chitosan-nanocatalyst complex/metal oxide precursor/polymers by electrospinning of the electrospinning solution, and the step S240 of fabricating metal oxide nanofibers in which nanocatalysts have been uniformly bound and functionalized by performing high-temperature thermal treatment on the synthesized complex nanofibers. Each of the steps is described more specifically below.

First, the step S210 of synthesizing chitosan-nanocatalyst complexes is described. A chitosan used in this step is a linear polysaccharide substance and has a property that it is combined with a metal ion in an aqueous state. One or two or more catalyst metal ions may be combined with such a chitosan, and a nanocatalyst of 1 to 100 nm in diameter can be formed through a reduction process. In order to combine the catalyst metal ions with the chitosans, the catalyst metal ions are combined with the chitosans by adding catalyst metal salts in an aqueous solution in which the chitosans have been dissolved. The catalyst metal ions are reduced to catalyst metal particles by adding a reducing agent. Representative metal salts used to combine the metal ions with the chitosans include platinum(IV) chloride, platinum(II) acetate, gold(I, III) chloride, gold(III) acetate, silver chloride, silver acetate, Iron(III) chloride, Iron(III) acetate, nickel(II) chloride, nickel(II) acetate, ruthenium(III) chloride, ruthenium acetate, iridium(III) chloride, iridium acetate, tantalum(V) chloride, palladium(II) chloride, lanthanum(III) acetate, copper(II) sulfate, and rhodium(III) chloride. The present invention is not limited to a specific metal salt if the metal salt includes metal ions which may be combined with chitosans. The metal ions combined using such metal salts are reduced to Pt, Au, Ag, Fe, Ni, Ru, Ir, Ta, Pd, La, Cu and Rh, etc. through a reducing process, thus forming chitosan-nanocatalyst complexes. A reducing agent for reducing the metal ions includes sodium borohydride ($NaBH_4$), lithium aluminum hydride ($LiAlH_4$), nascent (atomic) hydrogen, zinc-mercury amalgam (Zn(Hg)), oxalic acid ($C_2H_2O_4$), formic acid (HCOOH), ascorbic acid ($C_6H_8O_6$), sodium amalgam, diborane, and iron (II) sulfate. At least one reducing agent of the reducing agents is used. The catalyst particle of the formed chitosan-nanocatalyst complex has a nano size and shows excellent dispersibility due to a repulsive force between chitosans. Furthermore, the catalyst particle has a characteristic capable of adjusting the size of a metal particle depending on the type of metal salt, a concentration of chitosans and/or a concentration of metal salts.

Next, the step S220 of fabricating a electrospinning solution by mixing the synthesized chitosan-nanocatalyst complexes with a solution composed of a metal oxide precursor/polymers is described. In this step, after a metal oxide precursor/polymer solution are fabricated by dissolving the metal oxide precursor and polymers in a solvent, a chitosan-nanocatalyst complex/metal oxide precursor/polymer complex electrospinning solution is fabricated by adding the chitosan-nanocatalyst complexes, synthesized in the step S210, to the metal oxide precursor/polymer solution. In this case, the polymer is a template for forming nanofibers by performing electrospinning. Representative polymers used for the electrospinning include polymethylmethacrylate (PMMA), polyvinylpyrrolidone (PVP), polyvinyl acetate (PVAc), polyvinyl alcohol (PVA), polyacrylonitrile (PAN), polyethylene oxide (PEO), polypropylene oxide (PPO), polyethylene oxide copolymer, polypropylene oxide copolymer, polycarbonate (PC), polyvinyl chloride (PVC), polycaprolactone, and polyvinylidene fluoride. The present invention is not limited to a specific polymer if the polymer is capable of electrospinning. Furthermore, the metal oxide precursor used in this case is a precursor for forming metal oxide after being oxidized and crystallized through high-temperature thermal treatment. Representative metal oxide precursors include acetate, chloride, acetylacetonate, nitrate, methoxide, ethoxide, butoxide, isopropoxide, sulfide, etc. in which metal has been included. The present invention is not limited to a specific metal oxide precursor if the precursor can form metal oxide having a characteristic of a variable resistance type semiconductor gas sensor sensing material after high-temperature thermal treatment as described above. Furthermore, the solvent used to dissolve the metal oxide precursor and the polymers representatively includes N,N'-dimethylformamide, dimethylsulfoxide, N,N'-dimethylacetamide, N-methylpyrrolidone, deionized water, and ethanol. The present invention is not limited to a specific solvent if the solvent can dissolve both the metal oxide precursor and the polymers and can be electrospun. A concentration of the nanocatalysts of the chitosan-nanocatalyst complexes added in this step may be variously adjusted in the range of 0.001 to 50 wt % with respect to the metal oxide.

A process of fabricating the complex electrospinning solution includes adding the metal oxide precursor and the polymers to the solvent, stirring the mixture for 6 hours to 12 hours, and adding and mixing the aqueous solution including the chitosan-nanocatalyst complexes synthesized in the step S210. Finally, the chitosan-nanocatalyst complexes, the metal oxide precursor, and the polymers are stirred for 2 hours to 4 hours so that they are uniformly mixed in the solution.

Next, the step S230 of synthesizing the complex nanofibers composed of the chitosan-nanocatalyst complex/metal oxide precursor/polymers by electrospinning of the fabricated complex electrospinning solution is performed. In performing the electrospinning, after a syringe is filled with the chitosan-nanocatalyst complex/metal oxide precursor/polymer complex electrospinning solution synthesized in the step S220, the syringe is pushed at a constant rate using a syringe pump so that a specific amount of the electrospinning solution is discharged per unit time. An electrospinning system may include a high voltage generator, a grounded conductive substrate, a syringe, and a syringe pump. When an electric field of a high voltage (5 to 30 kV) is applied between the end of the needle of the syringe filled with a solution and the conductive substrate, an electrospinning solution discharged through the syringe needle is transformed into a nanofiber form and integrated on the conductive substrate. The discharge rate of the electrospinning solution may be adjusted between 0.01 ml/minutes to 0.5 ml/minutes. A complex nanofiber including chitosan-nanocatalyst complex/metal oxide precursor/polymers having a desired size can be fabricated by controlling the diameter or length of the nanofiber through control of a voltage and the amount of discharge. The electrospun nanofiber in this step has a characteristic in which the chitosan-nanocatalyst complexes have been uniformly distributed in the complex nanofiber due to the excellent dispersibility of the chitosan-nanocatalyst complexes.

Finally, the step S240 of fabricating metal oxide nanofibers in which nanocatalysts have been uniformly bound and functionalized by performing high-temperature thermal treatment on the synthesized complex nanofibers is performed. In this step, the metal oxide nanofibers in which catalysts have been functionalized are fabricated by thermally decomposing polymers and chitosans through high-temperature thermal treatment for the complex nanofibers synthesized in the step S230 and oxidizing and crystallizing the metal oxide precursor so that the nanocatalysts combined with the chitosans are uniformly bound to the nanofibers and functionalized. In this case, the nanocatalysts may be oxidized and transposed into at least one nanocatalyst of Pt, PtO, $PtO_2$, Au, $Au_2O_3$, Ag, $Ag_2O$, $Fe_2O_3$, NiO, $RuO_2$, $IrO_2$, $Ta_2O_5$, PdO, $PdO_2$, $La_2O_3$, CuO, and $Rh_2O_3$. The metal oxide precursor may be oxidized to include one or two or more complex materials selected from ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $ZrO_2$, $Al_2O_3$, $B_2O_3$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $Mn_{O2}$, $InTaO_4$, ITO, IZO, $InTaO_4$, MgO, $Ga_2O_3$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, and $Ba_{0.5}Sr_{0.5}Co_{0.8}Fe_{0.2}O_{3-7}$. In such a thermal treatment process, a thermal decomposition temperature of the chitosans is higher than a crystallization and particle growth temperature of the metal oxide precursor. Accordingly, chitosans chains that have been uniformly distributed suppress the growth of metal oxide particles, and the finally thermally decomposed chitosans leave fine pores in the nanofibers. Furthermore, an inorganic component naturally present in the chitosan is not decomposed in the thermal treatment process and remains as residues. The inorganic component of the chitosan representatively includes Mg, Fe, etc. The present invention is not limited to a specific inorganic matter if the inorganic matter can be generated in a process of extracting chitosans from the nature. Such an inorganic matter is oxidized after the thermal treatment to form MgO, $Fe_2O_3$, FeO and $Fe_3O_4$. The inorganic matter forms a heterojunction with metal oxide to expand the area of an electron depletion layer and to suppress the growth of particles of the metal oxide in the high-temperature thermal treatment process.

Figure 3:
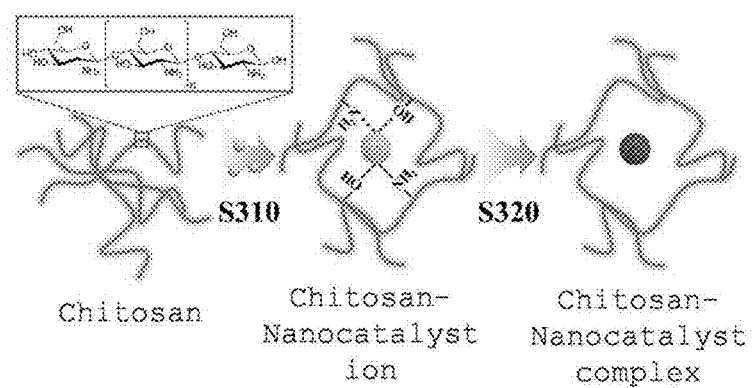
FIG. 3 is a diagram showing a synthesis process of chitosan-nanocatalyst complexes according to an embodiment of the present invention.

FIG. 3 schematically shows a synthesis process flow of a chitosan-nanocatalyst complex according to an embodiment of the present invention.

In step S310, that is, a first process, chitosans and catalyst metal ions are combined by adding metal salt, including catalyst metal ions, to an aqueous solution in which the chitosans have been dissolved.

Step S320, that is, a second process, is a process of reducing the catalyst metal ions to nanocatalysts particles by adding a reducing agent to the chitosan-catalyst metal ions synthesized in step S310. The synthesized nanocatalysts show excellent dispersibility due to a repulsive force between the chitosans.

Figure 4:
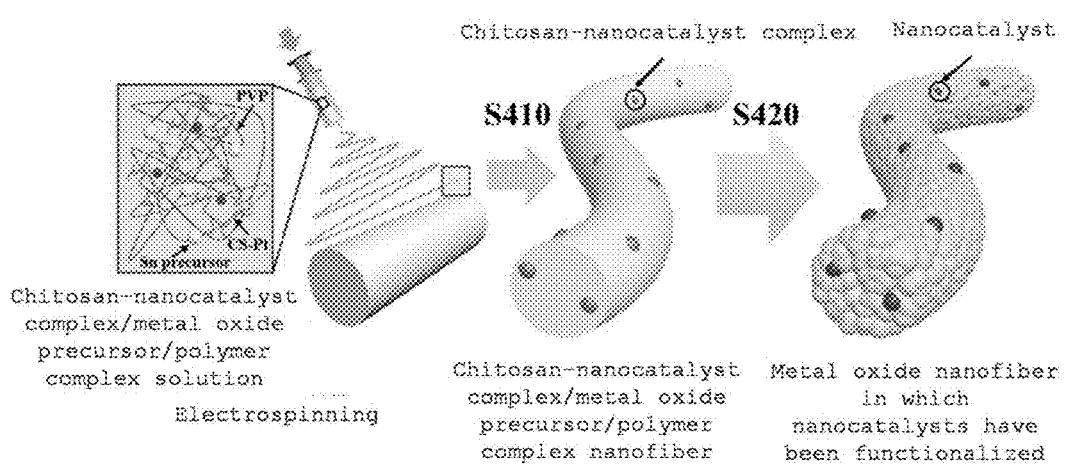
FIG. 4 is a diagram showing a process of fabricating a metal oxide nanofiber structure in which nanocatalysts have been uniformly bound and functionalized through electrospinning method and a thermal treatment process according to an embodiment of the present invention.

FIG. 4 schematically shows a fabrication process flow according to a method of fabricating a member for a gas sensor using metal oxide nanofibers in which catalysts have been functionalized, using electrospinning according to an embodiment of the present invention.

Step S410, that is, a first process, is an example in which a complex nanofiber in which chitosan-nanocatalyst complexes have been uniformly dispersed is fabricated by electrospinning of a complex electrospinning solution composed of chitosan-nanocatalyst complex/metal oxide precursor/polymers.

Step S420, that is, a second process, is a process of performing high-temperature thermal treatment on the complex nanofiber synthesized in step S410. The chitosans and the polymer are thermally decomposed, the metal oxide precursor is oxidized and crystallized, and nanocatalysts combined with the chitosans are uniformly bound to a metal oxide nanofiber.

The present invention is described in detail through embodiments and comparison examples. The embodiments and comparison examples are merely provided to describe the present invention and are not intended to limit the present invention to the following examples.

Embodiment 1: Fabrication of Chitosan with which Pt Nanocatalyst has been Combined First, a condition in which chitosans may be dissolved by adding acetic acid of 0.1 mL to DI water of 9.9 mL was formed. Thereafter, chitosans of 0.1 g were added and stirred at 300 rpm at room temperature for 12 hours or more so that the chitosans were fully dissolved. Thereafter, a separately prepared Pt precursor ($H_2PtCl_6 \cdot H_2O$) of 10 mg was added and stirred at 300 rpm at room temperature for 1 hour to 2 hours so that Pt ions were fully combined with the chitosans. Next, in order to reduce the Pt ions, combined with the chitosans, to Pt particles, a sodium borohydride ($NaBH_4$) aqueous solution (1 mol/L) was added and stirred at 300 rpm at room temperature for between 1 hour to 3 hours. The fabricated solution is used when an electrospinning solution is fabricated.

Figure 5:
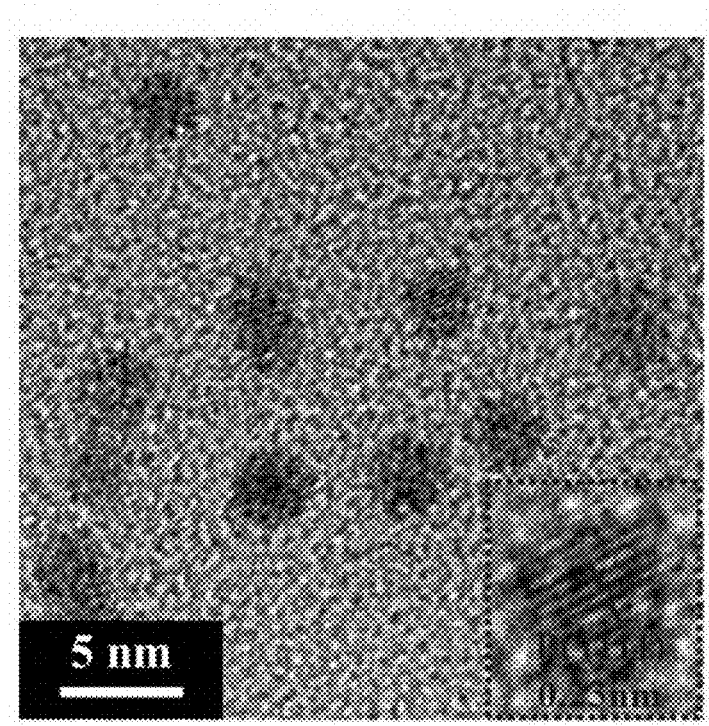
FIG. 5 shows an image of a transmission electron microscopy of chitosan-Pt nanocatalyst complexes according to embodiment 1 of the present invention.

FIG. 5 shows an image of a transmission electron microscopy of chitosans with which Pt nanoparticle catalysts fabricated by the process have been combined. From the drawing, it may be seen that the synthesized Pt nanoparticle has a size of about 3 nm and shows excellent dispersibility.

Embodiment 2: Fabrication of $SnO_2$ Nanofiber in which Pt Nanocatalysts were Uniformly Decorated and Functionalized Using Chitosan First, polyvinylpyrrolidone (PVP, molecular weight: 1,300,000 g/mol) of 0.35 g and a tin precursor ($SnCl_2 \cdot 2H_2O$) of 0.25 g were mixed with a DMF solution of 2 ml, and were stirred at 300 rpm at room temperature for 1 hour to 3 hours. Thereafter, the final complex electrospinning solution was fabricated by adding the chitosans-Pt nanocatalyst complexes solution of 60 μL, synthesized in the embodiment 1, to the stirred solution. After the fabricated electrospinning solution was moved to a syringe (Henke-Sass Wolf, 10 mL NORM-JECT®), the syringe was connected to a syringe pump, and the syringe pump was pushed at a discharge rate of 0.15 ml/minutes. When a high voltage of 15 kV was applied between a syringe needle (23 gauge) and stainless use steel, that is, a current collection plate, complex nanofibers composed of the chitosans-Pt nanocatalyst complexes/tin precursor/PVP were synthesized on the current collection plate.

Figure 6:
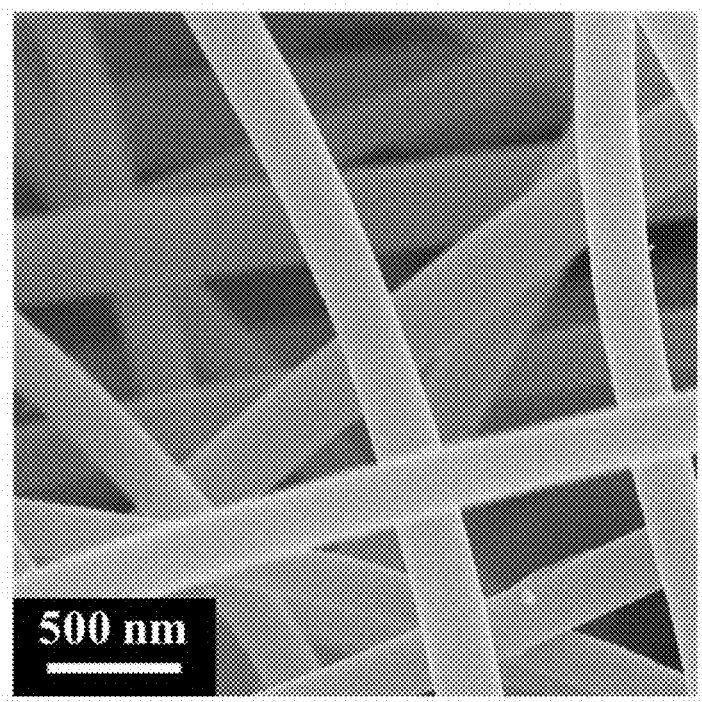
FIG. 6 shows an image of a scanning electron microscope of chitosan-Pt nanocatalyst complexes/polyvinylpyrolidone/tin oxide precursor complex nanofibers according to embodiment 2 of the present invention.

FIG. 6 shows an image of a scanning electron microscope for complex nanofibers composed of chitosan-Pt nanocatalyst complex/tin precursor/PVP collected after electrospinning. The composed nanofiber has a diameter in the range of 200 to 400 nm.

After the complex nanofibers composed of the chitosan-Pt nanocatalyst complex/tin precursor/PVP fabricated as described above were maintained at 600° C. for one hour at a heating rate of 5° C./minutes, they were cooled down to room temperature at a descending rate of 40° C./minutes. Thermal treatment was performed in the air atmosphere using the Vulcan 3-550 small electric furnace of Ney Co., Ltd. In this case, during the thermal treatment at 600° C., organic matters (chitosans, PVP) were decomposed, the tin precursor and the inorganic components of the chitosans were oxidized and crystallized, and Pt nanoparticle catalysts are bound to form functionalized $SnO_2$ nanofibers.

Figure 7:
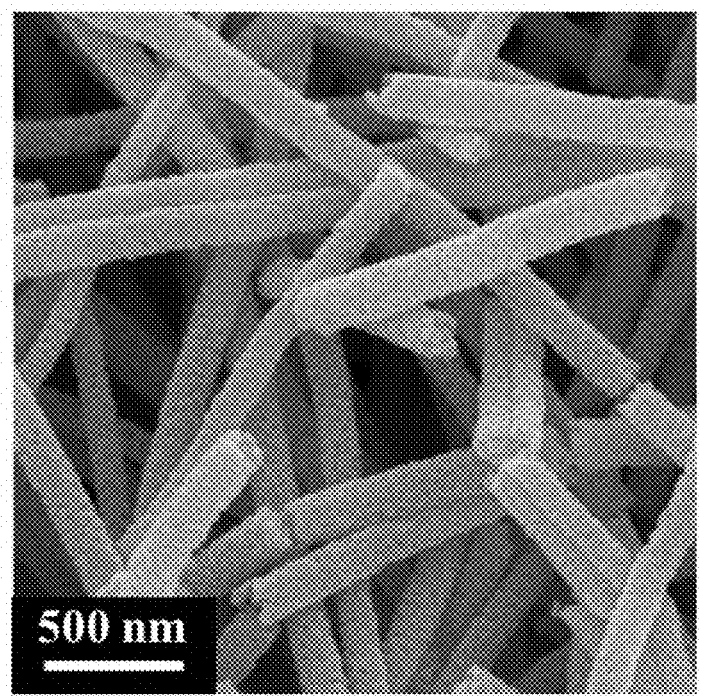
FIG. 7 shows an image of a scanning electron microscope of $SnO_2$ nanofibers in which Pt nanocatalysts have been uniformly bound and functionalized using chitosans, which have been synthesized after high-temperature thermal treatment, according to the embodiment 2 of the present invention.

FIG. 7 shows an image of a scanning electron microscope for the $SnO_2$ nanofibers in which the Pt nanoparticle catalysts synthesized in the embodiment 2 were bound and functionalized. The composed nanofiber has a reduced diameter of 150 to 350 nm as the organic matters are decomposed.

Figure 8:
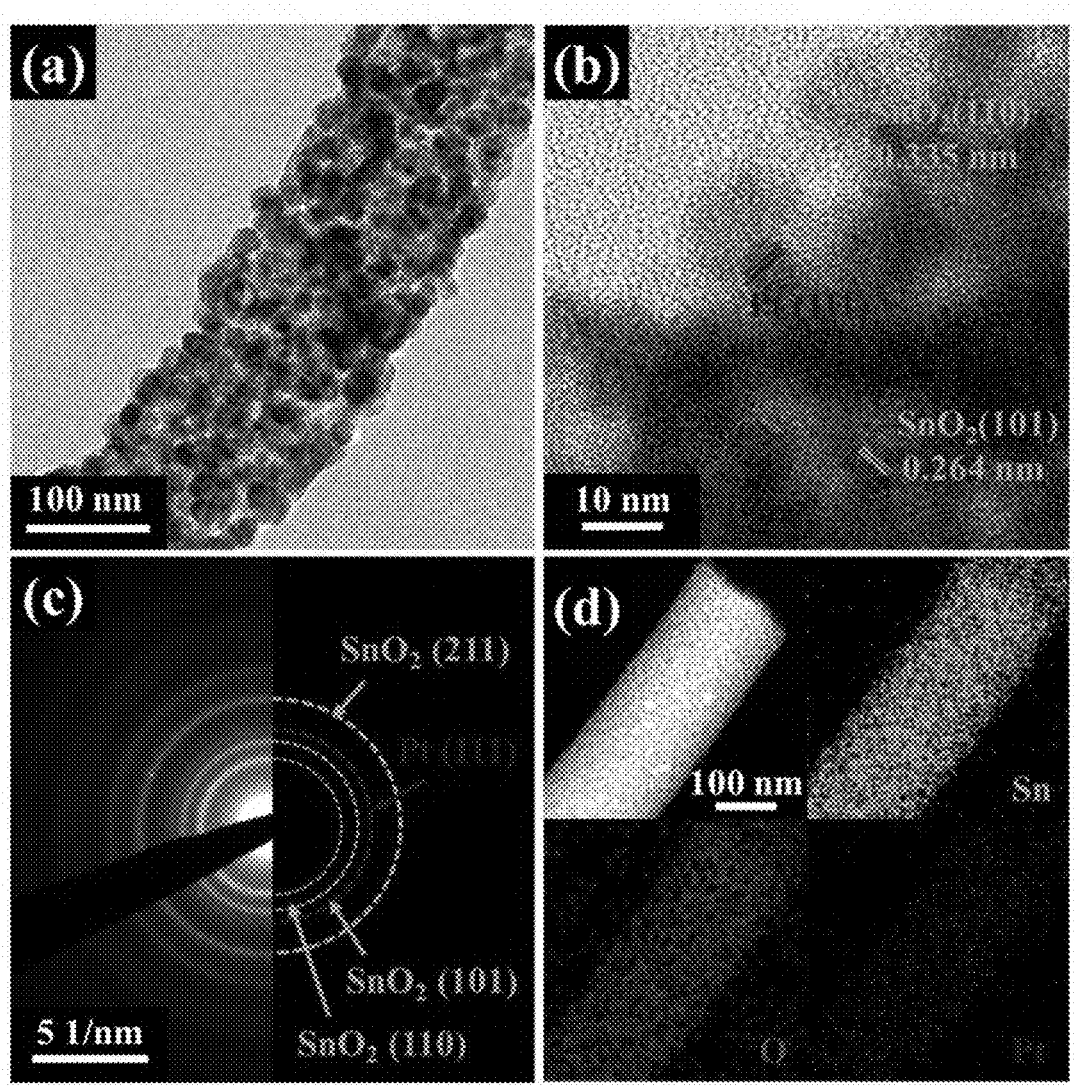
FIG. 8 shows an image of a transmission electron microscopy of SnO$_2$ nanofibers in which Pt nanocatalysts have been uniformly bound and functionalized using chitosans, which have been synthesized after high-temperature thermal treatment, according to the embodiment 2 of the present invention, and shows component analysis thereof.

FIG. 8 shows an image of a transmission electron microscopy of the $SnO_2$ nanofibers in which the Pt nanoparticle catalysts synthesized in the embodiment 2 were bound and functionalized, and the results of component analysis thereof. The image of the transmission electron microscopy clearly shows that pores are present in a nanofiber. Furthermore, an enlarged image of the transmission electron microscopy shows that the Pt nanoparticle catalyst has been bound to the $SnO_2$ nanofiber. Lattice analysis of the transmission electron microscopy shows the crystallizability of $SnO_2$ and the presence of Pt. Furthermore, it may be seen that Pt has been uniformly distributed in the $SnO_2$ nanofiber without cohesion through transmission electron microscopy component analysis (EDS).

Comparison Example 1. $SnO_2$ Nanofiber Synthesized Using Chitosan

A comparison example which may be compared with the embodiment 2 includes an $SnO_2$ nanofiber structure synthesized using chitosans. First, a condition in which chitosans may be dissolved by adding acetic acid of 0.1 mL to DI water of 9.9 mL was formed. Thereafter, chitosans of 0.1 g were added and stirred at 300 rpm at room temperature for 12 hours or more so that the chitosans were fully dissolved. Furthermore, PVP of 0.35 g and a tin precursor of 0.25 g were mixed with a DMF solution of 2 ml, and were stirred at 300 rpm at room temperature for 1 hour to 3 hours. The final complex electrospinning solution was fabricated by adding a chitosan solution of 60 μl to the stirred solution. After the fabricated electrospinning solution was moved to a syringe (Henke-Sass Wolf, 10 mL NORM-JECT‖), the syringe was connected to a syringe pump, and the syringe pump was pushed at a discharge rate of 0.15 ml/minutes. When a high voltage of 15 kV was applied between a syringe needle (23 gauge) and stainless use steel, that is, a current collection plate, complex nanofibers composed of the chitosan/tin precursor/PVP were synthesized on the current collection plate. After the complex nanofibers composed of the chitosan/tin precursor/PVP was maintained at a heating rate of 5° C./minutes at 600° C. for one hour, they were cooled to room temperature at a descending rate of 40° C./minutes. Thermal treatment was performed in the air atmosphere using the Vulcan 3-550 small electric furnace of Ney Co., Ltd. During the thermal treatment of 600° C., PVP was thermally decomposed, organic matter components of the chitosans were decomposed to leave pores in the nanofibers, and inorganic components of the chitosans were oxidized to form heterojunctions with metal oxide. Accordingly, $SnO_2$ nanofibers in which the tin precursor was oxidized and crystallized were synthesized.

Figure 9:
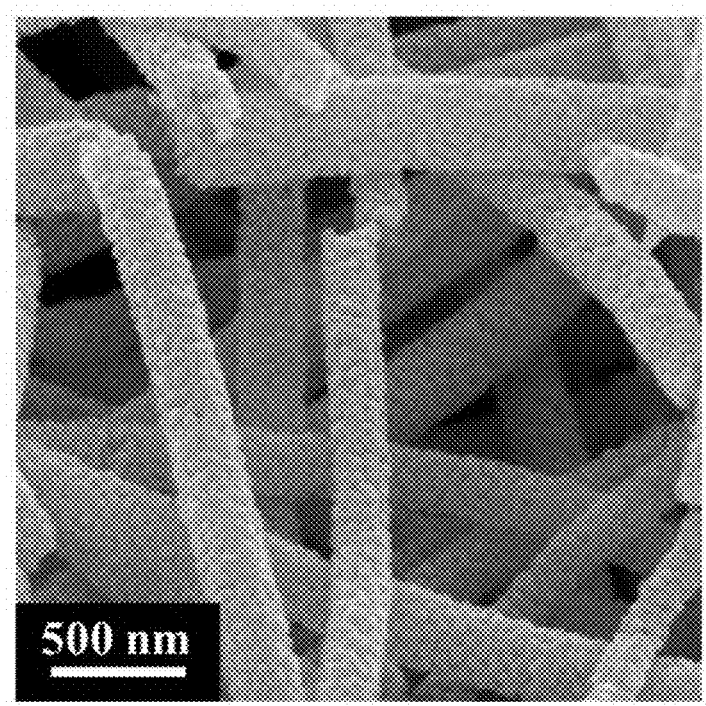
FIG. 9 shows an image of a scanning electron microscope of SnO$_2$ nanofibers synthesized using chitosans according to a comparison example 1 of the present invention.

FIG. 9 shows an image of a scanning electron microscope of the $SnO_2$ nanofibers synthesized using chitosans fabricated in comparison example 1. An average diameter of the synthesized $SnO_2$ nanofibers is about 300 nm.

The $SnO_2$ nanofibers synthesized using the fabricated chitosans were used for a comparison between sensing characteristics for a variety of gases along with the $SnO_2$ nanofibers in which the Pt nanocatalysts were uniformly bound and functionalized using chitosans fabricated in the embodiment 2.

Comparison Example 2. $SnO_2$ Nanofiber

A comparison example which may be compared with the embodiment 2 includes pristine $SnO_2$ nanofibers. PVP of 0.35 g and a tin precursor of 0.25 g were mixed with a DMF solution of 2 ml and were stirred at 300 rpm at room temperature for 3 hours to 6 hours. After the fabricated electrospinning solution was moved to a syringe (Henke-Sass Wolf, 10 mL NORM-JECT®), the syringe was connected to a syringe pump, and the syringe pump was pushed at a discharge rate of 0.15 ml/minutes. When a high voltage of 15 kV was applied between a syringe needle (23 gauge) and stainless steel, that is, a current collection plate, complex nanofibers composed of the tin precursor/PVP were synthesized on the current collection plate.

After the complex nanofibers composed of the tin precursor/PVP fabricated using the above method was maintained at 600° C. at a heating rate of 5° C./minutes for one hour, they were cooled down to room temperature at a descending rate of 40° C./minutes. Thermal treatment was performed in the air atmosphere using the Vulcan 3-550 small electric furnace of Ney Co., Ltd. In this case, during the thermal treatment at 600° C., the organic matter (PVP) was decomposed and the tin precursor was oxidized and crystallized to form the $SnO_2$ nanofibers.

Figure 10:
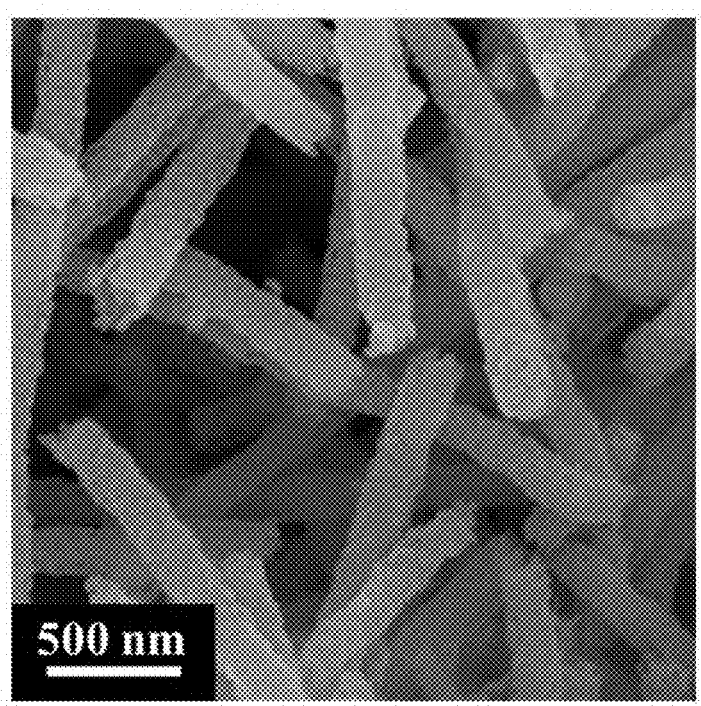
FIG. 10 shows an image of a scanning electron microscope of SnO$_2$ nanofibers according to a comparison example 2 of the present invention.

FIG. 10 shows an image of a scanning electron microscope for the $SnO_2$ nanofibers fabricated in the comparison example 2. An average diameter of the synthesized $SnO_2$ nanofibers is about 250 nm.

The fabricated $SnO_2$ nanofibers were used for a comparison between sensing characteristics for a variety of gases along with the $SnO_2$ nanofibers in which the Pt nanocatalysts were uniformly bound and functionalized using chitosans fabricated in the embodiment 2.

Experiment Example 1. Check a Change in Mass and a Degree of Heat Transfer According to Thermal Treatment of Chitosans and Analysis of Residues As may be seen from the images of the scanning electron microscopes, the nanofiber fabricated in the comparison example 2 shows a particle size of about 20 nm. In contrast, the nanofiber fabricated in the embodiment 2 shows a small particle size of about 10 nm. In order to check the reason, a change in mass and a degree of heat transfer according to the thermal treatment of the chitosans used in the embodiment 2 were checked. Furthermore, an attempt was made to check that the inorganic components of the chitosan remained as residues through a change in mass. Chitosans of about 50 mg were thermally treated from room temperature up to 700° C. in the air atmosphere at a heating rate of 5° C./minutes, a change in mass and a degree of heat transfer were checked, and components remained as residues were analyzed.

Figure 11:
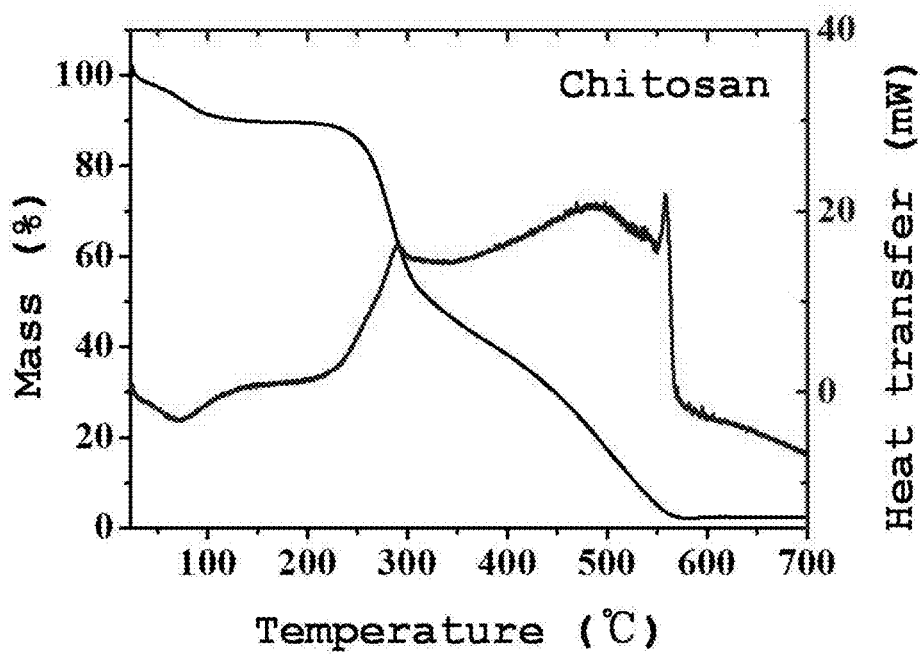
FIG. 11 is an experiment example 1 of the present invention, and is a graph showing a change in mass and a degree of heat transfer according to temperatures when chitosans are thermally treated.

FIG. 11 is a graph showing a change in mass and a degree of heat transfer according to the thermal treatment of the chitosans used in the embodiment 2, according to the experiment example 1 of the present invention. As may be seen from the graph, the chitosans were decomposed about 40% at 400° C. or more. When considering that the crystallization of the tin oxide precursor starts at 400° C., chitosans remained at a temperature of 400° C. or more may suppress the growth of $SnO_2$ particles. That is, $SnO_2$ having a small particle size is formed because the growth of $SnO_2$ particles is suppressed by the chitosans. Furthermore, it may be seen that the mass of the chitosans does not reach 0% at 600° C. or more. Residues of about 2.5% are left. Accordingly, it can be seen that inorganic components are included in the chitosans and such inorganic components continuously suppress the growth of metal oxide particles during the 1-hour thermal treatment at 600° C.

Figure 12:
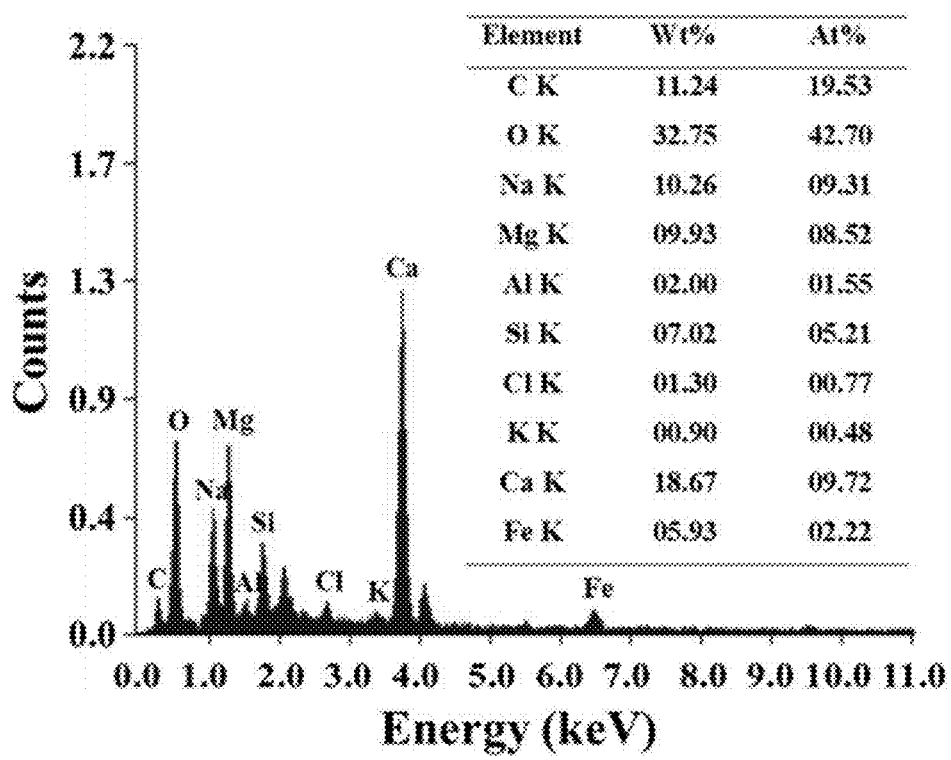
FIG. 12 shows component analysis of residues left over after chitosans are thermally treated and an image of a transmission electron microscopy according to the experiment example 1 of the present invention.
Figure 12:
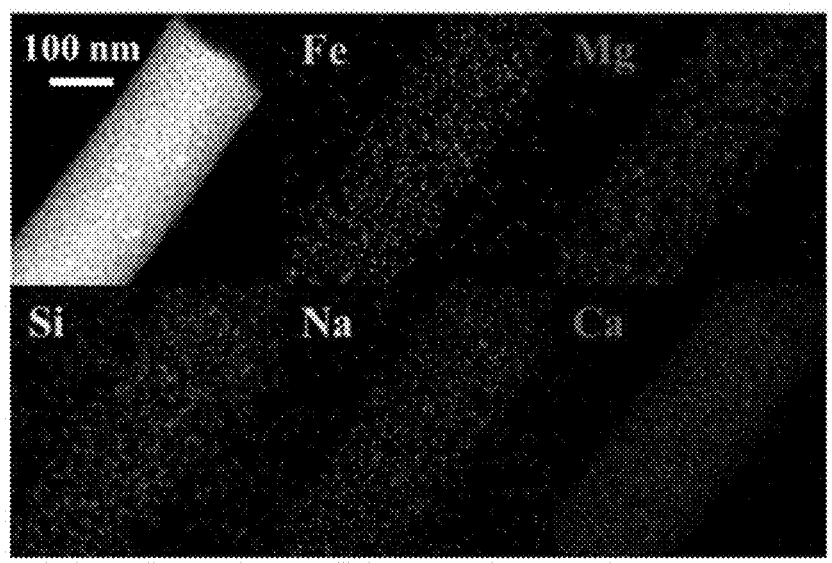

FIG. 12 shows a component analysis table of chitosan residues and an image of a scanning electron microscope. It may be seen that Fe, Mg, Si, Na and Ca, etc. derived in the process of extracting the chitosans were uniformly distributed in the nanofibers. The elements suppress the growth of metal oxide particles in the thermal treatment process and also form heterojunctions with metal oxide by forming oxide, thus playing an electronic sensitizer role.

Experiment Example 2. Fabrication of Gas Sensors Using $SnO_2$ Nanofibers in which Pt Nanocatalysts were Uniformly Bound and Functionalized Using Chitosans, $SnO_2$ Nanofibers Synthesized Using Chitosans, and $SnO_2$ Nanofibers and Characteristic Evaluation Thereof In order to use the sensing materials, fabricated in the embodiment 2 and the comparison examples 1 and 2, for gas sensors for exhaled breath analysis, 5 mg of each of the $SnO_2$ nanofibers in which the Pt nanocatalysts were uniformly bound and functionalized using chitosans, the $SnO_2$ nanofibers synthesized using chitosans, and the $SnO_2$ nanofibers was dispersed in ethanol 250 μL and subjected to a grinding process through ultrasonic cleaning for 1 hour. Thereafter, each of the $SnO_2$ nanofibers in which the Pt nanocatalysts were uniformly bound and functionalized using chitosans, the $SnO_2$ nanofibers synthesized using chitosans, and the $SnO_2$ nanofibers dispersed in ethanol was dropped and coated on an alumina ($Al_2O_3$) substrate of 3 mm×3 mm in size on which parallel gold (Au) electrodes were patterned using a micropipette. A process of drying the $SnO_2$ nanofibers on a hot-plate of 60° C. was performed. Such a process was repeated 3 to 5 times so that a sufficient amount of nanofibers was uniformly coated on the alumina sensor substrate.

In order to evaluate the characteristic of each fabricated gas sensor, an acetone sensing characteristic was evaluated by maintaining the operating temperature of the sensor to 350° C. in a high humidity environment (90% RH) and to change a concentration of acetone ($CH_3COCH_3$) gas to 5, 4, 3, 2, 1, 0.6, 0.4, 0.2, 0.1 ppm. Furthermore, in the experiment example 2, a selective gas sensing ability was evaluated by evaluating a sensing characteristic for ethanol ($C_2H_5OH$), hydrogen sulfide ($H_2S$), formaldehyde (HCHO), toluene ($C_6H_5CH_3$), carbon monoxide (CO), methane ($CH_4$), and ammonia ($NH_3$), in addition to the acetone gas, that is, a representative example of a volatile organic compound gas.

Figure 13:
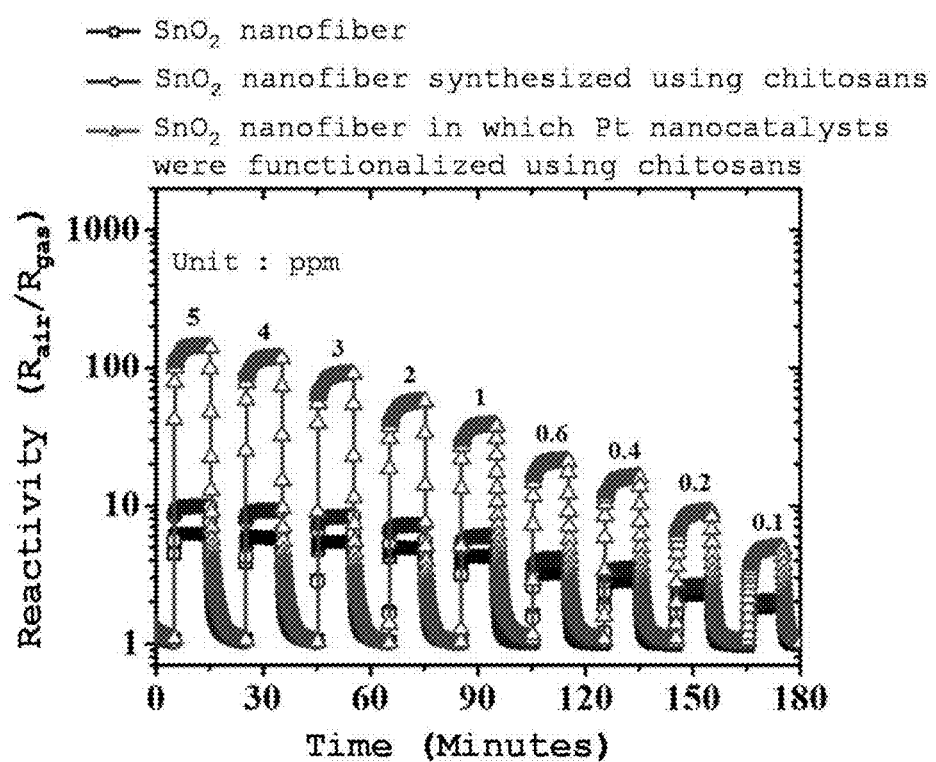
FIG. 13 is experiment example 2 of the present invention, and is a reactivity graph of gas sensors based on the SnO$_2$ nanofibers synthesized using chitosans, the SnO$_2$ nanofibers in which Pt nanocatalysts have been functionalized, and SnO$_2$ nanofibers according to the embodiment 2 and comparison examples 1 and 2 at 350° C. with respect to acetone gas (0.1-5 ppm).

FIG. 13 shows the measurement of reactivity ($R_{air}/R_{gas}$, wherein $R_{air}$ is a resistance value of the gas sensor when air was injected, $R_{gas}$ is a resistance value of the gas sensor when the acetone gas was injected) while decreasing a concentration of the acetone gas from 5 ppm to 0.1 ppm at 350° C. over time. As shown in FIG. 13, the $SnO_2$ nanofibers in which the Pt nanocatalysts were uniformly bound and functionalized using chitosans has a sensitivity characteristic, which is 14 times or higher improvement than that of pristine $SnO_2$ nanofibers synthesized using chitosans and the $SnO_2$ nanofibers with respect to the acetone gas of 5 ppm. This clearly shows an effect of the uniformly dispersed Pt nanocatalysts. Furthermore, the reactivity of the $SnO_2$ nanofibers synthesized using chitosans has sensitivity about 70% more improved than the pristine $SnO_2$ nanofibers. This evidences a small particle size according to the chitosans, an electronic sensitizer role of oxide formed through the oxidation of inorganic components of the chitosans, and easy diffusion of gas through the pores formed when the chitosans are decomposed.

Figure 14:
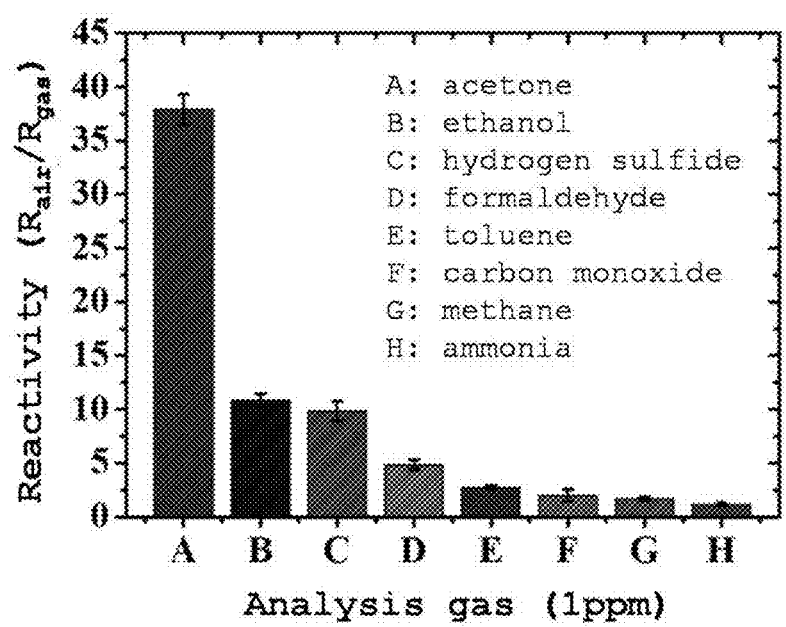
FIG. 14 is experiment example 2 of the present invention, and shows sensitivity characteristics of the gas sensor based on SnO$_2$ nanofibers in which Pt nanocatalysts have been functionalized using chitosans according to the embodiment 2 at 350° C. with respect to gases (e.g., acetone, ethanol, hydrogen sulfide, formaldehyde, toluene, carbon monoxide, methane, and ammonia) of 1 ppm.

FIG. 14 shows reactivity of the $SnO_2$ nanofibers in which the Pt nanocatalysts were uniformly bound and functionalized using chitosans with respect to acetone, ethanol, hydrogen sulfide, formaldehyde, toluene, carbon monoxide, methane, and ammonia 1 ppm, which were measured at 350° C. As shown in FIG. 14, it may be seen that a gas sensor based on the $SnO_2$ nanofibers in which the Pt nanocatalysts were uniformly bound and functionalized using chitosans shows reactivity less than about 10.5 for ethanol, hydrogen sulfide, formaldehyde, toluene, carbon monoxide, methane, and ammonia gas, but shows a very excellent reactivity of about 38 for acetone. Accordingly, it could be seen that the gas sensor has a selective gas sensing ability.

Figure 15:
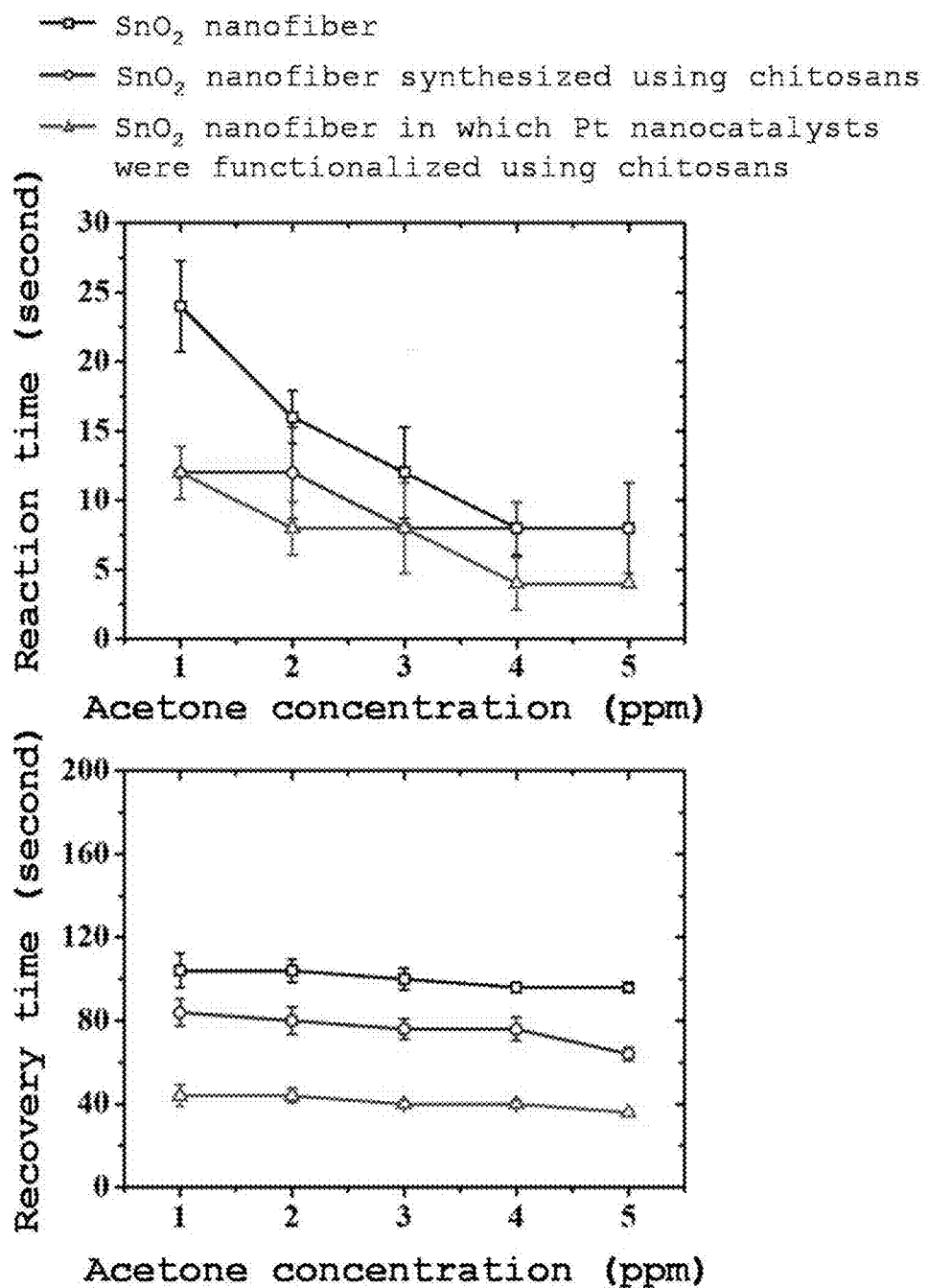
FIG. 15 is experiment example 2 of the present invention, and shows characteristic evaluation results of gas sensors based on the SnO$_2$ nanofibers in which Pt nanocatalysts have been functionalized using chitosans, the SnO$_2$ nanofibers synthesized using chitosans, and SnO$_2$ nanofibers according to the embodiment 2 and the comparison examples 1 and 2 at 350° C. when a concentration of acetone is 1, 2, 3, 4, and 5 ppm with respect to reaction speed and recovery speed of the gas sensor.

FIG. 15 shows the results of characteristic evaluation of gas sensors based on the $SnO_2$ nanofibers in which the Pt nanocatalysts were uniformly bound and functionalized using chitosans, the $SnO_2$ nanofibers synthesized using chitosans, and the known $SnO_2$ nanofibers with respect to reaction speeds and recovery speeds when a concentration of acetone was 1, 2, 3, 4, and 5 ppm at 350° C. As shown in the results, it may be seen that the response speed of the $SnO_2$ nanofibers in which the Pt nanocatalysts were uniformly bound and functionalized using chitosans is very fast, that is, within 12 seconds, but the reaction speed of the known nanofiber structure is relatively slow, that is, 24 seconds. Such results evidence that a gas reaction is accelerated by the Pt nanocatalysts and a small particle size and the formation of pores are achieved by the Pt nanocatalysts, and that a fast gas reaction is induced by inducing an instantaneous change in resistance through the electronic sensitization role of oxide of the chitosan inorganic components. Furthermore, it may be seen that the recovery speed of the $SnO_2$ nanofibers in which the Pt nanocatalysts were uniformly bound and functionalized using chitosans is very fast, that is, within 44 seconds, but the recovery speed of the known nanofiber structure is relatively slow, that is, within 104 seconds. It may be seen that such results lead to fast recovery because the attachment and detachment of gas are accelerated by the Pt nanocatalysts.

The experiment example shows the sensor characteristics of the gas sensor based on the $SnO_2$ nanofibers in which the Pt nanocatalysts were uniformly bound and functionalized using chitosans, which has high sensitivity, a high reaction speed, and selectivity for acetone. Furthermore, a change in the gas selectivity characteristic may be expected by changing the type of nanoparticle catalyst and metal oxide material. Accordingly, a variety of metal oxide nanofibers to which a variety of nanoparticle catalyst particles have been bound can be synthesized, and a gas sensor array having high sensitivity and selectivity for a variety of types of gases can be fabricated. A metal oxide nanofiber sensing material including the nanoparticle catalysts realized through the chitosans may be used for a healthcare gas sensor for the gas analysis and diagnosis of organic compounds within expiration.

Embodiment 3: Fabrication of $SnO_2$ Nanostructure in which NiO and $Fe_2O_3$ are Uniformly Bound and Functionalized Using Chitosans First, polyvinylpyrrolidone (PVP, molecular weight: 1,300,000 g/mol) of 0.3 g and a tin precursor ($SnCl_2.2H_2O$) of 0.25 g were mixed with a DMF solution of 2 ml, and was stirred at 300 rpm at room temperature for 1 hour to 3 hours. In this case, the reason why a small amount of PVP of 0.3 g was used is to easily synthesize nanostructures including nanofibers within a nanotube after thermal treatment. Thereafter, the final complex electrospinning solution was fabricated by adding a chitosan-Ni/Fe dual nanocatalyst complex solution of 40 μL to the stirred solution. After the fabricated electrospinning solution was moved to a syringe (Henke-Sass Wolf, 10 mL NORM-JECT"), the syringe was connected to a syringe pump, and the syringe pump was pushed at a discharge rate of 0.15 ml/minutes. When a high voltage of 15 kV was applied between a syringe needle (23 gauge) and stainless use steel, that is, a current collection plate, complex nanofibers composed of the chitosan-Ni/Fe dual nanocatalyst complex/tin precursor/PVP was synthesized on a current collection plate.

Figure 16:
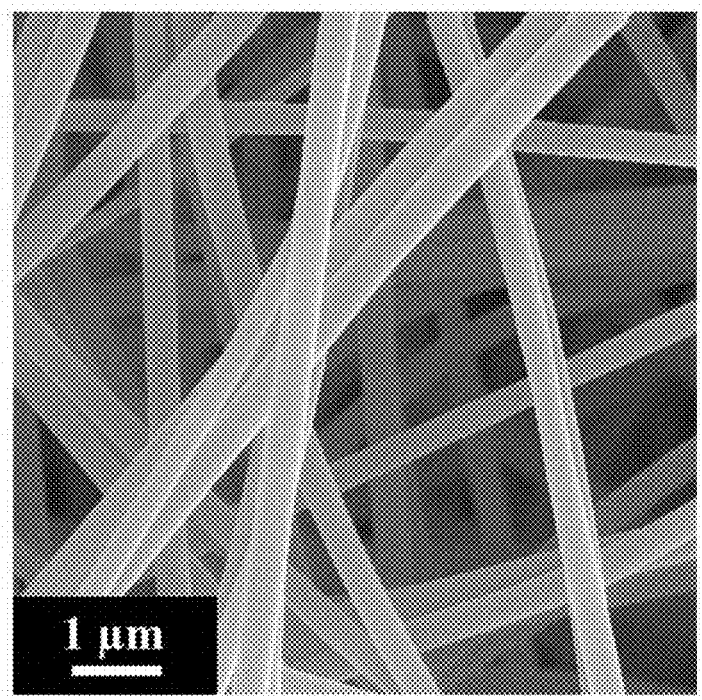
FIG. 16 shows an image of a scanning electron microscope of chitosan-Ni/Fe dual nanocatalyst complexes/polyvinylpyrrolidone/tin oxide precursor complex nanofibers according to an embodiment 3 of the present invention.

FIG. 16 shows an image of a scanning electron microscope of a chitosan-Ni/Fe dual nanocatalyst complex/polyvinylpyrrolidone/tin oxide precursor complex nanostructure collected after electrospinning.

After the chitosan-Ni/Fe dual nanocatalyst complex/polyvinylpyrolidone/tin oxide precursor complex nanofibers fabricated using the method was maintained at a heating rate of 5° C./minutes at 600° C. for one hour, they were cooled down to room temperature at a descending rate of 40° C./minutes. Thermal treatment was performed in the air atmosphere using the Vulcan 3-550 small electric furnace of Ney Co., Ltd. In this case, during the thermal treatment of 600° C., organic matters (chitosans, PVP) were decomposed, the tin precursor and the inorganic components of the chitosans were oxidized and crystallized, and Ni and Fe nanoparticle catalysts were oxidized to form the $SnO_2$ nanostructures in which NiO and $Fe_2O_3$ were uniformly bound and functionalized.

Figure 17:
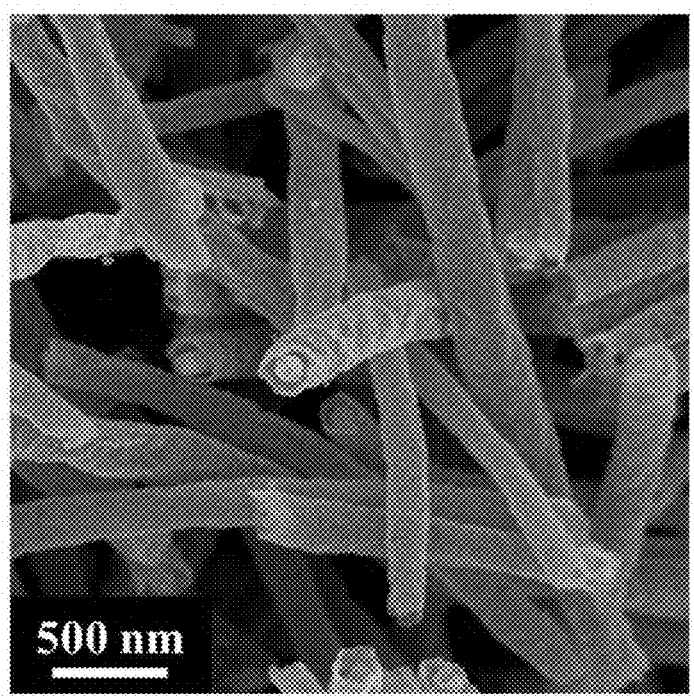
FIG. 17 shows an image of a scanning electron microscope of SnO$_2$ nanostructures in which NiO and Fe$_2$O$_3$ have been uniformly bound and functionalized using chitosans, which have been synthesized after high-temperature thermal treatment, according to the embodiment 3 of the present invention.

FIG. 17 shows an image of a scanning electron microscope of the $SnO_2$ nanostructures in which NiO and $Fe_2O_3$ were uniformly bound and functionalized, which was synthesized in the embodiment 3.

Figure 18:
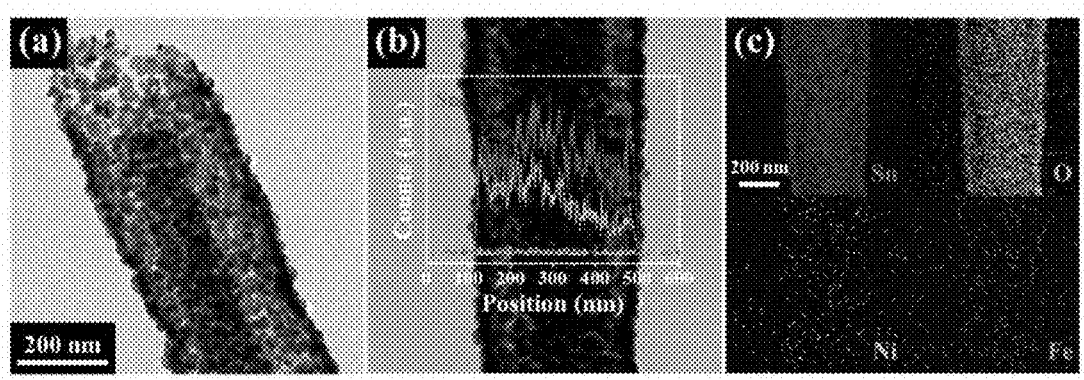
FIG. 18 shows pictures of transmission electron microscopy and component analysis of SnO$_2$ nanostructures in which NiO and Fe$_2$O$_3$ have been uniformly bound and functionalized using chitosans, which have been synthesized after high-temperature thermal treatment, according to the embodiment 3 of the present invention.

FIG. 18 shows an image of a transmission electron microscopy of the $SnO_2$ nanostructures in which NiO and $Fe_2O_3$ were uniformly bound and functionalized, which was synthesized in the embodiment 3, and the results of component analysis thereof. The image of the transmission electron microscopy clearly shows a nanostructure shape including a nanofiber within a nanotube. Furthermore, the line analysis graph of the transmission electron microscopy shows a form in which nanofibers decreased from the outside and increased again within the inside depending on a nanostructure shape in which the nanofibers are present within the nanotube. Furthermore, it can be seen that NiO and $Fe_2O_3$ are uniformly distributed in the $SnO_2$ nanostructure without cohesion through transmission electron microscopy component analysis (EDS).

Comparison Example 3. $SnO_2$ Nanostructure

A comparison example which may be compared with the embodiment 3 includes an $SnO_2$ nanostructure. The final complex electrospinning solution was fabricated by mixing PVP of 0.30 g and a tin precursor of 0.25 g with a DMF solution of 2 ml and stirring the mixture at 300 rpm at room temperature for 3 hours to 6 hours. In this case, the reason why a small amount of PVP of 0.3 g was used is to easily synthesize a nanostructure in which a nanofiber is present in a nanotube after thermal treatment. After the fabricated electrospinning solution was moved to a syringe (Henke-Sass Wolf, 10 mL NORM-JECT®), the syringe was connected to a syringe pump, and the syringe pump was pushed at a discharge rate of 0.15 ml/minutes. When a high voltage of 15 kV was applied between a syringe needle (23 gauge) and stainless use steel, that is, a current collection plate, complex nanofibers composed of the tin precursor/PVP was synthesized on the current collection plate.

After the complex nanofibers compose of the tin precursor/PVP fabricated using the method was maintained at 600° C. at a heating rate of 5° C./minutes for one hour, they were cooled down to room temperature at a descending rate of 40° C./minutes. Thermal treatment was performed in the air atmosphere using the Vulcan 3-550 small electric furnace of Ney Co., Ltd. In this case, during the thermal treatment at 600° C., an organic matter (PVP) was decomposed and the tin precursor was oxidized and crystallized to form the nanostructure in which the nanofiber was present in the $SnO_2$ nanotube.

Figure 19:
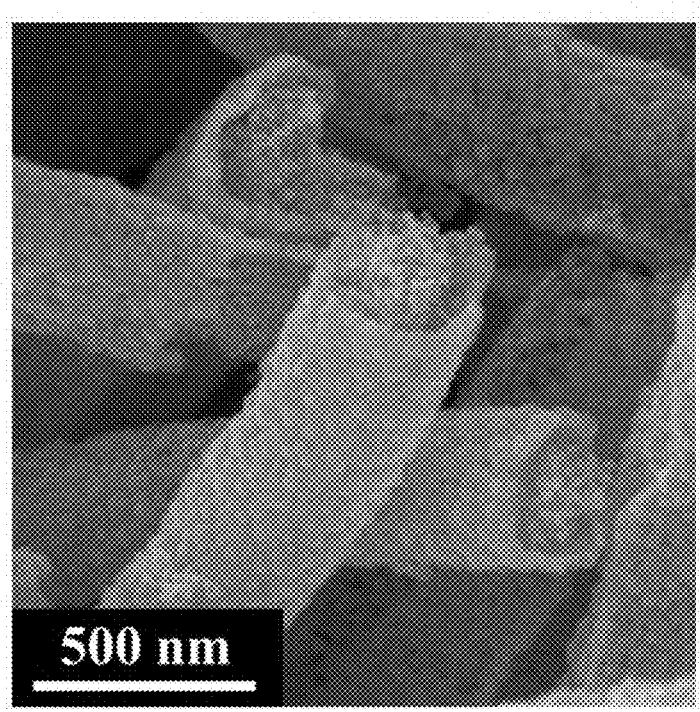
FIG. 19 shows an image of a scanning electron microscope of SnO$_2$ nanostructures according to comparison example 3 of the present invention.

FIG. 19 shows an image of a scanning electron microscope of the $SnO_2$ nanostructure fabricated in the comparison example 3.

The fabricated $SnO_2$ nanostructure was used for a comparison between the sensing characteristics of a variety of gases along with the $SnO_2$ nanostructure in which NiO and $Fe_2O_3$ were uniformly bound and functionalized using chitosans fabricated in the embodiment 3.

Experiment Example 3. Fabrication of Gas Sensor Using $SnO_2$ Nanostructure in which NiO and $Fe_2O_3$ were Uniformly Bound and Functionalize Using Chitosans and Known $SnO_2$ Nanostructure and Characteristic Evaluation Thereof In order for the sensing materials, fabricated in the embodiment 3 and the comparison example 3, for gas sensors, after 5 mg of each of the $SnO_2$ nanostructure in which NiO and $Fe_2O_3$ were uniformly bound and functionalized using chitosans and the known $SnO_2$ nanostructure was dispersed in ethanol 250 µL, $SnO_2$ nanostructure was fabricated into a short fiber by sonicating tin oxide nanostructure through ultrasonication for one hour. Thereafter, after each of the $SnO_2$ nanostructure solution in which NiO and $Fe_2O_3$ were uniformly bound and functionalized and the known $SnO_2$ nanostructure solution dispersed in ethanol was dropped and coated on an alumina ($Al_2O_3$) substrate of 3 mm×3 mm in size on which parallel gold (Au) electrodes were patterned using a micropipette, a process of drying the $SnO_2$ nanostructure solution on a hot-plate of 60° C. was performed. Such a process was repeated 3 to 5 times so that a sufficient amount of nanofibers was uniformly coated on the alumina sensor substrate.

In order to evaluate the characteristics of the fabricated gas sensor, a formaldehyde sensing characteristic was evaluated by maintaining the operating temperature of the sensor to 350° C. in an environment (30% RH) similar to the inside of a building and changing a concentration of formaldehyde (HCHO) gas to 5, 4, 3, 2, 1, 0.6, 0.4, and 0.2 ppm. Furthermore, in the experiment example 3, a selective gas sensing ability was evaluated by evaluating the sensing characteristic of toluene ($C_6H_5CH_3$), ethanol ($C_2H_5OH$), xylene ($C_6H_4(CH_3)_2$), hydrogen sulfide ($H_2S$), pentane ($CH_3(CH_2)_3CH_3$), ammonia ($NH_3$) and carbon monoxide (CO) in addition to formaldehyde gas, that is, a representative example of a sick house syndrome-causing gas.

Figure 20:
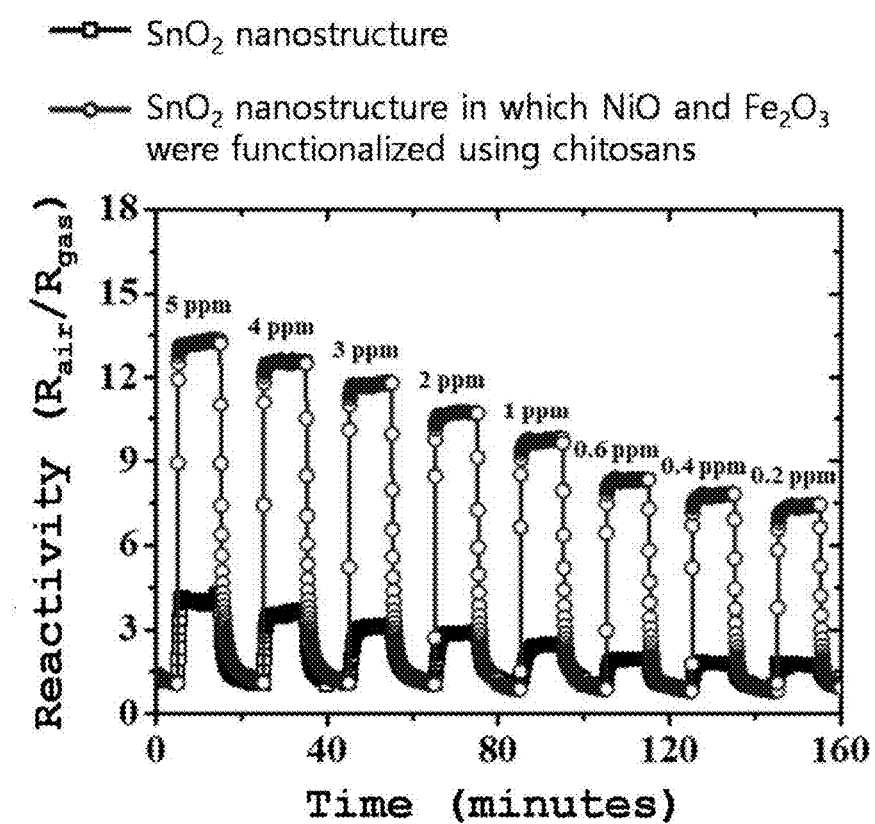
FIG. 20 is an experiment example 3 of the present invention, and is a reactivity graph of gas sensors based on the SnO$_2$ nanostructures in which NiO and Fe$_2$O$_3$ have been uniformly bound and functionalized using chitosans and known SnO$_2$ nanostructures according to the embodiment 3 and the comparison example 3 at 350° C. with respect to formaldehyde gas (0.2-5 ppm).

FIG. 20 shows the measurement of reactivity ($R_{air}/R_{gas}$, wherein $R_{air}$ is a resistance value of the gas sensor when air was injected, $R_{gas}$ is a resistance value of the gas sensor when the formaldehyde gas was injected) while decreasing the concentration of the formaldehyde gas from 5 ppm to 0.2 ppm at 350° C. over time. As shown in FIG. 20, the $SnO_2$ nanostructure in which NiO and $Fe_2O_3$ were uniformly bound and functionalized using chitosan has a sensitivity characteristic that is 5 times or more improved compared to the known $SnO_2$ nanostructure with respect to the formaldehyde gas of 0.2 ppm. This clearly shows the dual sensitization effect of the uniformly dispersed $NiO/Fe_2O_3$ catalyst. Furthermore, this evidences a small particle size according to the chitosans, the electronic sensitizer role of oxide formed through the oxidation of inorganic components of the chitosans, and each gas diffusion through the pores formed through the decomposition of the chitosan.

Figure 21:
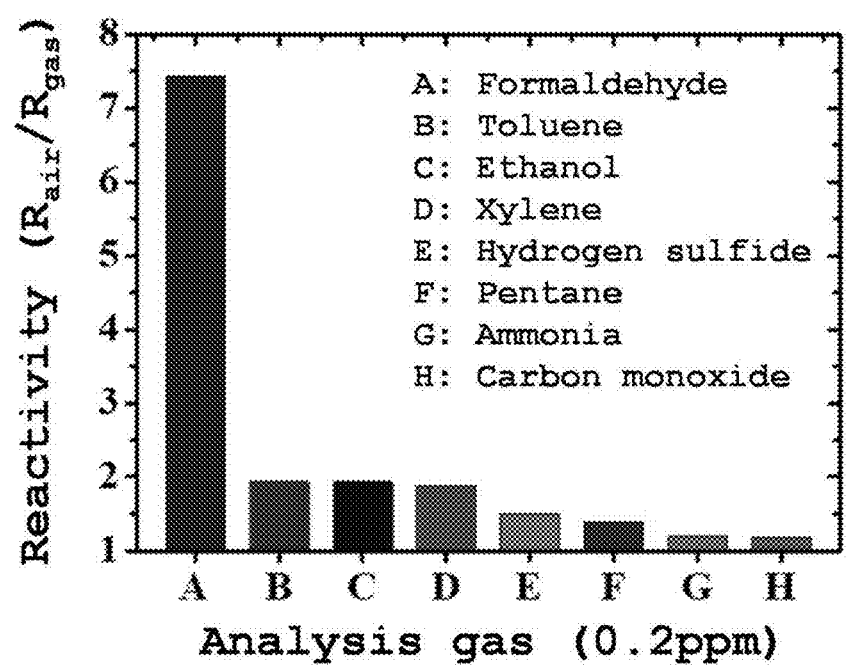
FIG. 21 is an experiment example 3 of the present invention, and shows sensitivity characteristics of a gas sensor based on the SnO$_2$ nanostructures in which NiO and Fe$_2$O$_3$ have been uniformly bound and functionalized using chitosans according to the embodiment 3 at 350° C. with respect to gases (e.g., formaldehyde, toluene, ethanol, xylene, hydrogen sulfide, pentane, ammonia, carbon monoxide) of 0.2 ppm.

FIG. 21 shows reactivity of the $SnO_2$ nanostructure in which NiO and $Fe_2O_3$ were uniformly bound and functionalized using chitosan, which were measured at 350° C., with respect to formaldehyde, toluene, ethanol, xylene, hydrogen sulfide, pentane, ammonia, and carbon monoxide of 0.2 ppm. As shown in FIG. 21, it can be seen that the gas sensor based on the $SnO_2$ nanostructure in which NiO and $Fe_2O_3$ were uniformly bound and functionalized using chitosan has reactivity less than 2 for the toluene, ethanol, xylene, hydrogen sulfide, pentane, ammonia, and carbon monoxide gas, but has a very excellent sensitivity of about 7.5 for formaldehyde, and thus has a selective formaldehyde gas sensing ability.

Figure 22:
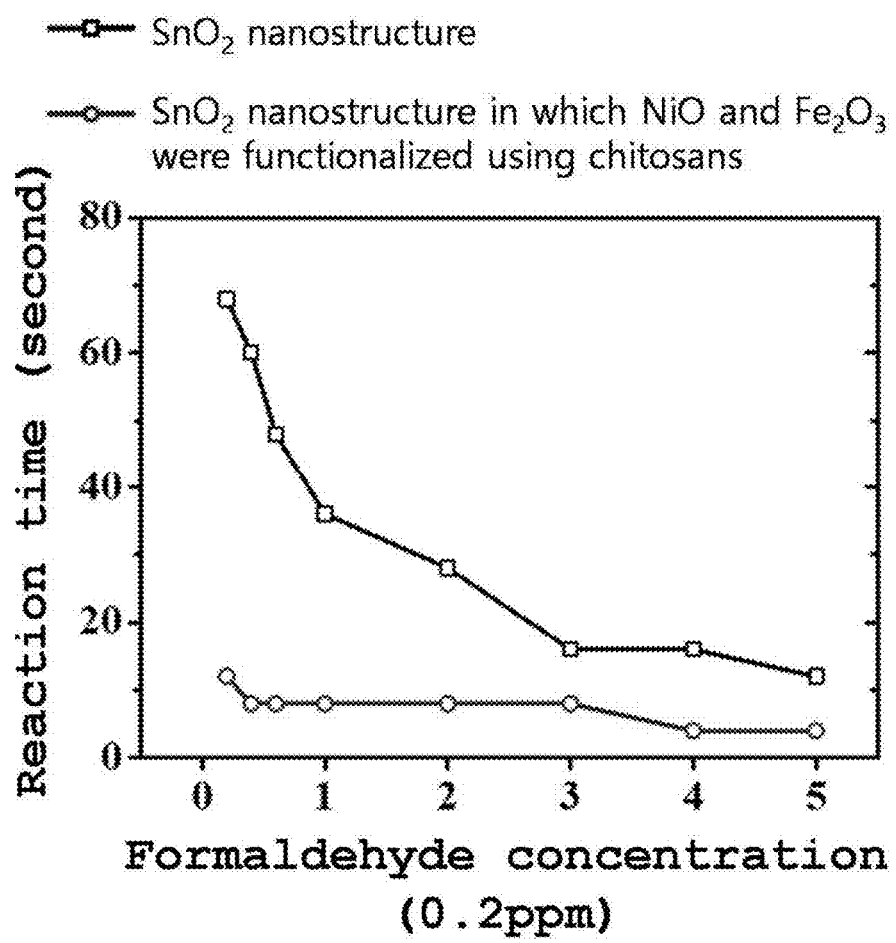
FIG. 22 is an experiment example 3 of the present invention, and shows characteristic evaluation results of gas sensors based on the SnO$_2$ nanostructures in which NiO and Fe$_2$O$_3$ have been uniformly bound and functionalized using chitosans and the known SnO$_2$ nanostructures according to the embodiment 3 and the comparison example 3 at 350° C. when a concentration of formaldehyde is 0.2, 0.4, 0.6, 1, 2, 3, 4, and 5 ppm with respect to reaction speed of the gas sensor.

FIG. 22 shows the results of characteristic evaluation of the gas sensors based on the $SnO_2$ nanostructure in which NiO and $Fe_2O_3$ were uniformly bound and functionalized using chitosans and the known $SnO_2$ nanostructure at 350° C. when a concentration of formaldehyde was 0.2, 0.4, 0.6, 1, 2, 3, 4, and 5 ppm. As shown in the results, it can be seen that the reaction speed of the $SnO_2$ nanostructure in which NiO and $Fe_2O_3$ were uniformly bound and functionalized using chitosans is very fast within 12 seconds for formaldehyde of 0.2 ppm, but the reaction speed of the known nanostructure is relatively very slow, that is, within 68 seconds. Such results evidence that a gas reaction is accelerated by the dual sensitizer of NiO and $Fe_2O_3$, a small particle size, the formation of pores, and that a fast gas reaction is induced by deriving an instantaneous change in resistance by the electronic sensitization role of oxide of the chitosan inorganic components.

The experiment example shows the sensor characteristics of the gas sensor based on the $SnO_2$ nanostructure in which NiO and $Fe_2O_3$ were uniformly bound and functionalized using chitosan, which has high sensitivity, a high reaction speed, and selectivity for formaldehyde. Furthermore, a change in the gas selectivity characteristic can be expected by changing the number and type of nanoparticle catalysts and the type of metal oxide material. Accordingly, a variety of metal oxide nanofibers to which a variety of nanoparticle catalyst particles have been bound can be synthesized, and a gas sensor array having high sensitivity and selectivity for a variety of types of gases can be fabricated. The metal oxide nanofiber sensing material including the nanoparticle catalysts realized through the chitosans may be used for a real-time air quality monitoring system for gas analysis of indoor air and diagnosis of air quality.

According to the embodiments of the present invention, if the metal oxide nanofibers in which the catalysts have been functionalized are synthesized using the chitosan-nanocatalyst complexes according to a catalyst binding method, the nanocatalysts uniformly bound to the nanofibers provide an electronic or chemical sensitization effect, and an excellent catalyst effect can be expected because cohesion does not occur between catalyst particles even at high operating temperatures. Accordingly, the metal oxide nanofiber sensing material having high sensitivity and a selective sensing ability can be fabricated. Furthermore, the chitosans increase the ratio of an electron depletion layer area formed on a surface of particles by suppressing the growth of metal oxide particles in a high-temperature thermal treatment process, increase reactivity by increasing a change in resistance depending on whether gas is present, widens the active site of the sensing material by facilitating the diffusion of gas through the formation of the pores in the nanofibers, and significantly increase a sensing characteristic because oxides formed through the oxidation of inorganic components remained as the residues of the chitosans form heterojunctions with metal oxide to play an electronic sensitizer role. The present method is a method of fabricating a gas sensor, which has not been conventionally proposed and has a very high effect through a cheap and simple process. Accordingly, the member for a gas sensor having high sensitivity, a selective sensing ability, stability, and a fast reaction speed, the gas sensor, and the method of fabricating the same can be provided.

The above description is merely a description of the technical spirit of the present invention, and those skilled in the art may change and modify the present invention in various ways without departing from the essential characteristic of the present invention. Accordingly, the embodiments disclosed in the present invention should not be construed as limiting the technical spirit of the present invention, but should be construed as illustrating the technical spirit of the present invention. The scope of the technical spirit of the present invention is not restricted by the embodiments, and the range of protection of the present invention should be interpreted based on the following appended claims.

What is claimed is:

1. A metal oxide nanofiber comprising functionalized catalysts, wherein metal is bound to an inside and a surface in nano size and functions as a catalyst through high-temperature thermal treatment of a complex nanofiber comprising chitosan-metal complexes, a metal oxide precursor, and polymers, wherein the chitosan of the chitosan-metal complex naturally contains an inorganic component in a process of extracting the chitosan from a shell of a crustacean and synthesizing the chitosan.

2. The metal oxide nanofibers of claim 1, wherein metal particles of the chitosans-metal complex are configured with one or two or more metals included in a range of 1 to 100 nm in diameter through bonding with a chitosan.

3. The metal oxide nanofibers of claim 1, wherein metal particles of the chitosans-metal complex are uniformly bound to a nanofiber and functionalized through dispersibility according to a repulsive force between chitosans.

4. The metal oxide nanofibers of claim 1, wherein the chitosan is thermally decomposed through high-temperature thermal treatment of the complex nanofiber and forms pores having a size range of 1 to 50 nm in the nanofiber.

5. The metal oxide nanofibers of claim 1, wherein in the high-temperature thermal treatment process of the complex nanofiber, a thermal decomposition temperature of the chitosan is higher than the crystallization temperature of the metal oxide precursor, the chitosans uniformly distributed in the complex nanofiber suppress a growth of metal oxide particles, and components remaining as residues after the chitosan is decomposed continue to suppress a growth of metal oxide particles.

6. The metal oxide nanofibers of claim 1, wherein in the high-temperature thermal treatment process of the complex nanofiber, inorganic components included in the chitosan form heterojunctions with metal oxide.

7. The metal oxide nanofibers of claim 1, wherein wt % of the metal included in the chitosans-metal complex is included in a range of 0.001 to 50 wt % with respect to the metal oxide.

8. The metal oxide nanofibers of claim 1, wherein the chitosans-metal complex is formed by combining the chitosan with metal ions by adding one or two or more metal salts selected from acetate, nitrate, chloride, acetylacetonate, methoxide, ethoxide, butoxide, isopropoxide, and sulfide to a solution in which the chitosan has been dissolved and reducing the metal ions to one or two or more metal particles through reduction treatment.

9. The metal oxide nanofibers of claim 1, wherein the metal oxide nanofiber is configured with one or two or more complex metal oxide materials selected from ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $ZrO_2$, $Al_2O_3$, $B_2O_3$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $MnO_2$, $InTaO_4$, ITO, IZO, $InTaO_4$, MgO, $Ga_2O_3$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, and $Ba_{0.5}Sr_{0.5}Co_{0.8}Fe_{0.2}O_{3-7}$.

10. A gas sensor comprising a sensor electrode on which metal oxide nanofibers comprising functionalized catalysts have been coated and capable of measuring a change in resistance, wherein metal is bound to an inside and a surface in nano size and functions as a catalyst through high-temperature thermal treatment of a complex nanofiber comprising chitosan-metal complexes, a metal oxide precursor, and polymers.

* * * * *